(12) United States Patent
Blelloch et al.

(10) Patent No.: US 9,790,557 B2
(45) Date of Patent: Oct. 17, 2017

(54) METHODS AND SYSTEMS FOR DETERMINING A LIKELIHOOD OF ADVERSE PROSTATE CANCER PATHOLOGY

(71) Applicant: The Regents of the University of California, Oakland, CA (US)

(72) Inventors: Robert Hector Blelloch, San Francisco, CA (US); Siao-Yi Wang, Long Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/686,593

(22) Filed: Apr. 14, 2015

(65) Prior Publication Data

US 2015/0211077 A1 Jul. 30, 2015

Related U.S. Application Data

(63) Continuation of application No. PCT/US2013/068126, filed on Nov. 1, 2013.

(60) Provisional application No. 61/721,699, filed on Nov. 2, 2012.

(51) Int. Cl.
  *C12Q 1/68* (2006.01)
  *C07H 21/04* (2006.01)
  *G06F 19/00* (2011.01)

(52) U.S. Cl.
  CPC ....... *C12Q 1/6886* (2013.01); *G06F 19/3431* (2013.01); *G06F 19/3487* (2013.01); *C12Q 2600/112* (2013.01); *C12Q 2600/118* (2013.01); *C12Q 2600/158* (2013.01); *C12Q 2600/166* (2013.01); *C12Q 2600/178* (2013.01)

(58) Field of Classification Search
  None
  See application file for complete search history.

(56) References Cited

U.S. PATENT DOCUMENTS

| | | | |
|---|---|---|---|
| 2008/0182239 A1* | 7/2008 | Mullinax | C12Q 1/6811 435/6.14 |
| 2008/0254481 A1* | 10/2008 | Love | G01N 33/564 435/7.1 |
| 2009/0298701 A1* | 12/2009 | Baker | C12Q 1/6886 506/7 |
| 2010/0113290 A1 | 5/2010 | Klass et al. | |
| 2010/0297652 A1* | 11/2010 | Shelton | C12Q 1/6886 435/6.1 |
| 2011/0275534 A1 | 11/2011 | Cohn et al. | |
| 2012/0028264 A1* | 2/2012 | Shak | C12Q 1/6886 435/6.14 |
| 2012/0264638 A1 | 10/2012 | Brase et al. | |

FOREIGN PATENT DOCUMENTS

| | | | |
|---|---|---|---|
| WO | 2009143379 | | 11/2009 |
| WO | WO 2011/021177 | * | 2/2011 |
| WO | WO 2011/080315 | * | 7/2011 |

OTHER PUBLICATIONS

Esteller (Nature Reviews Genetic vol. 12 Dec. 2011 pp. 861-874).*
Krell et al. Frontiers in Bioscience (Elite Edition), vol. 5, pp. 204-213, Jan. 2013; e.g., Abstract.*
McShane et al. British Journal of Cancer, vol. 93, pp. 387-391, 2005.*
Liang (BMC Genomics 2007, 8:166 pp. 1-20).*
Ason (PNAS Sep. 26, 2006 vol. 103 No. 39 pp. 14385-14389).*
Moltzahn (Cancer Res vol. 71 No. 2 pp. 550-560 Jan. 15, 2011).*
Moltzahn (Cancer Res vol. 71 No. 2 pp. 550-560 Jan. 15, 2011 pre-pub online Nov. 22, 2010 plus supplementary tables).*
Little, et al., (2012) "Multigene Panels in Prostate Cancer Risk Assessment" Evidence Report/Technology Assessment; 209, 8 pages.
Albertsen et al. (2005) "20-Year Outcomes Following Conservative Management of Clinically Localized Prostate Cancer," JAMA; 293:2095-2101.
Auvinen et al. (1996) "Screening for Prostate Cancer Using Serum Prostate-Specific Antigen: a Randomised, Population-Based Pilot Study in Finland," British Journal of Cancer; 74:568-572.
Bissels et al. (2009) "Absolute quantification of microRNAs by using a universal reference," RNA; 15(12):2375-2384.
Cooperberg (2010) "Understanding and Applying Rish Assesment for Prostate Cancer," PCRI Insights; 13(4):3-7.
Cooperberg, M et al. (2005) "The UCSF Cancer of the Prostate Risk Assessment (CAPRA) Score: a Straightforward and Reliable Preoperative Predictor of Disease Recurrence After Radical Prostatectomy," J Urol.; 173(6):1938-1942.
Cronin et al. (2004) "Universal RNA Reference Materials for Gene Expression," Clin. Chem; 50(8):1464-1471.
Duttagupta et al. (2011) "Impact of Cellular miRNAs on Circulating miRNA Biomarker Signatures," PLoS One; 6(6):e20769.
Galiveti et al. (2010) "Application of housekeeping npcRNAs for quantitative expression analysis of human transcriptome by real-time PCR," RNA; 16(2):450-461.
Hassan et al. (2012) "Recent Updates on the Role of microRNAs in Prostate Cancer," Journal of Hematology & Oncology; 5(9):1-10.
Heidenreich et al. (2008) "EAU Guidelines on Prostate Cancer," Eur Urol; 53:68-80.

(Continued)

*Primary Examiner* — Amanda Haney
(74) *Attorney, Agent, or Firm* — Carol L. Francis; Bozicevic, Field & Francis LLP

(57) ABSTRACT

The present disclosure provides methods that find use in determining a likelihood of adverse prostate cancer pathology in a subject. The methods generally involve detection of one or more diagnostic microRNAs (miRNAs), such as mir-19a, mir-19b, mir-519c-5p, and/or mir-345 in a biological sample from the subject, such as blood or blood product. The detection of one or more such diagnostic miRNAs can be used to determine a likelihood of adverse prostate cancer pathology in a subject. The methods of the present disclosure also find use in facilitating treatment decisions for a subject. Also provided are devices, systems, and kits that may be used in practicing methods of the present disclosure.

11 Claims, 33 Drawing Sheets

(56) References Cited

OTHER PUBLICATIONS

Hothron, et al. (2006) "Unbiased Recursive Partitioning: A Conditional Inference Framework," J. Comp. and Graph. Stat.; 15:651-674.

Kirschner et al. (2011) "Haemolysis during Sample Preparation Alters microRNA Content of Plasma," PLoS One; 6(9):e24145.

Kozomara and Griffiths-Jones (2011) "miRBase: integrating microRNA annotation and deep-sequencing data," Nucleic Acids Res.; 39(Database Issue):D152-D157.

Mestdagh et al. (2009) "A novel and universal method for microRNA RT-qPCR data normalization," Genome Biol.; 10(6):R64.

Meyer et al. (2012) "Profound Effect of Profiling Platform and Normalization Strategy on Detection of Differentially Expressed Micro RNAs—A Comparative Study," PLoS One; 7(6):e38946.

Mitchell et al. (2008) "Circulating microRNAs as stable blood-based markers for cancer detection," PNAS; 105(30):10513-10518.

McCall and Irizarry (2008) "Consolidated strategy for the analysis of microarray spike-in data," Nucleic Acids Res.; 36(17): e108.

Moltzahn et al. (2011) "High Throughput MicroRNA Profiling: Optimized Multiplex qRT-PCR at Nanoliter Scale on the Fluidigm Dynamic Array™ IFCs," J. Vis. Exp.; (54):e2552.

Moltzahn, et al. (2011) "Microfluidic based multiplex qRT-PCR identifies diagnostic and prognostic microRNA signatures in sera of prostate cancer patients," Cancer Res.; 71:550-560.

Peltier and Latham (2008) "Normalization of microRNA expression levels in quantitative RT-PCR assays: Identification of suitable reference RNA targets in normal and cancerous human solid tissues," RNA; 14(5):844-852.

Roa et al. (2010) "Identification of a new microRNA expression profile as a potential cancer screening tool," Clin Invest Med; 33(2):e124-e132.

Schaefer et al. (2010) "Suitable reference genes for relative quantification of miRNA expression in prostate cancer," Exp. Mol. Med.; 42(11):749-758.

Shariat et al. (2008) "An Updated Catalog of Prostate Cancer Predictive Tools," Cancer; 113(11):3075-3099.

Shariat et al. (2008) "Inventory of prostate cancer predictive tools," Curr. Opin. Urol.; 18(3):279-296.

Timoneda et al. (2012) "Determination of Reference microRNAs for Relative Quantification in Porcine Tissues," PLoS One; 7(9):e44413.

Wylie et al. (2011) "A novel mean-centering method for normalizing microRNA expression from high-throughput RT-qPCR data," BMC Res Notes; 4:555.

Suardi et al. (2008) "Currently Used Criteria for Active Surveillance in Men With Low-risk Prostate Cancer," Cancer; 113:2068-2072.

* cited by examiner

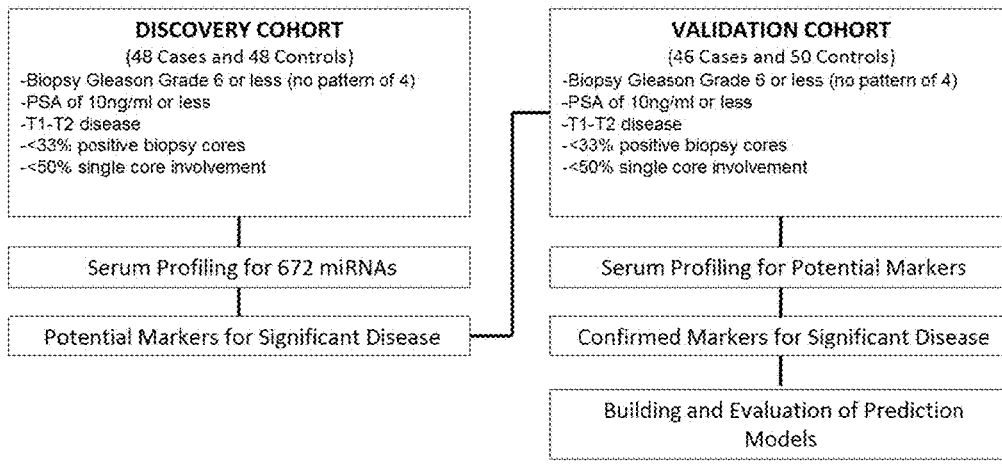

FIG. 3

| MicroRNA | MicroRNA Cluster or Family |
|---|---|
| mir-17 | mir-17-92 cluster |
| mir-19a | mir-17-92 cluster |
| mir-20a | mir-17-92 cluster |
| mir-19b | mir-17-92/106a-363 clusters |
| mir-92a | mir-17-92/106a-363 clusters |
| mir-106a | mir-106a-363 cluster |
| mir-93 | mir-106b-25 cluster |
| mir-25 | mir-106b-25 cluster |
| let-7b | let-7 cluster |
| mir-24 | mir-181c/23b clusters |
| mir-939 | mir-1234 cluster |
| mir-1234 | mir-1234 cluster |
| mir-519c-5p | mir-1283 cluster |
| mir-522 | mir-1283 cluster |
| mir-525-5p | mir-1283 cluster |
| mir-660 | mir-188 cluster |
| mir-941 | mir-1914 cluster |
| mir-1274a | mir-1274 cluster |
| mir-1274b | mir-1274 cluster |
| mir-302f | mir-302 family |
| mir-34c-3p | mir-34 family |
| mir-663 | mir-663 family |
| mir-197 | |
| mir-223 | |
| mir-297 | |
| mir-345 | |
| mir-346 | |
| mir-484 | |
| mir-486 | |
| mir-584 | |
| mir-638 | |
| mir-629 | |
| mir-720 | |
| mir-942 | |
| mir-1208 | |
| mir-1243 | |

A

| miRNA* | OR** | 95% CI (P) | AUC† | 95% CI (P‡) |
|---|---|---|---|---|
| mir-19a | 4.21 | 1.1, 14.75 (0.024) | 0.73 | 0.62, 0.83 (0.22) |
| mir-19b | 5.68 | 2.00, 16.15 (<0.001) | 0.77 | 0.67, 0.86 (0.07) |
| mir-345 | 0.12 | 0.04, 0.42 (0.001) | 0.77 | 0.68, 0.87 (0.04) |
| mir-519c-5p | 0.21 | 0.08, 0.52 (0.001) | 0.76 | 0.67 0.86 (0.09) |

B

| miRNA* | OR** | 95% CI (P) | AUC† | 95% CI (P‡) |
|---|---|---|---|---|
| mir-19a | 8.78 | 3.23, 23.95 (<0.001) | 0.81 | 0.72, 0.90 (0.016) |
| mir-19b | 10.37 | 3.74, 28.78 (<0.001) | 0.83 | 0.74, 0.91 (0.007) |
| mir-345 | 0.43 | 0.13, 1.40 (0.16) | 0.71 | 0.58, 0.79 (0.181) |
| mir-519c-5p | 0.07 | 0.02, 0.24 (<0.001) | 0.82 | 0.74, 0.91 (0.006) |

|  | CAPRA | | | Total |
| --- | --- | --- | --- | --- |
|  | 0 | 1 | 2 |  |
| Control | 9 | 28 | 13 | 50 |
|  | 90.0% | 50.0% | 43.3% | 52.1% |
| Cases | 1 | 28 | 17 | 46 |
|  | 10.0% | 50.0% | 56.7% | 47.9% |
| Total | 10 | 56 | 30 | 96 |

B

|  | miRNA + CAPRA | | | | | Total |
| --- | --- | --- | --- | --- | --- | --- |
|  | 1 | 2 | 3 | 4 | 5 |  |
| Control | 21 | 14 | 8 | 7 | 0 | 50 |
|  | 91.3% | 63.6% | 44.4% | 30.4% | 0.0% | 52.1% |
| Cases | 2 | 8 | 10 | 16 | 10 | 46 |
|  | 8.7% | 36.4% | 55.6% | 69.6% | 100.0% | 47.9% |
| Total | 23 | 22 | 18 | 23 | 10 | 96 |

FIG. 12

| MicroRNA | MicroRNA Cluster or Family |
|---|---|
| miR-17 | miR-17-92 cluster |
| miR-19a | miR-17-92 cluster |
| miR-20a | miR-17-92 cluster |
| miR-19b | miR-17-92/106a-363 clusters |
| miR-92a | miR-17-92/106a-363 clusters |
| miR-106a | miR-106a-363 cluster |
| miR-93 | miR-106b-25 cluster |
| miR-25 | miR-106b-25 cluster |
| let-7b | let-7 cluster |
| miR-24 | miR-181c/23b clusters |
| miR-939 | miR-1234 cluster |
| miR-1234 | miR-1234 cluster |
| miR-519c-5p | miR-1283 cluster |
| miR-522 | miR-1283 cluster |
| miR-525-5p | miR-1283 cluster |
| miR-660 | miR-188 cluster |
| miR-941 | miR-1914 cluster |
| miR-1274a | miR-1274 cluster |
| miR-1274b | miR-1274 cluster |
| miR-302f | miR-302 family |
| miR-34c-3p | miR-34 family |
| miR-663 | miR-663 family |
| miR-197 | |
| miR-223 | |
| miR-297 | |
| miR-345 | |
| miR-346 | |
| miR-484 | |
| miR-486 | |
| miR-584 | |
| miR-638 | |
| miR-629 | |
| miR-720 | |
| miR-942 | |
| miR-1208 | |
| miR-1243 | |

FIG. 13

| | DISCOVERY COHORT (n = 96) | | | |
|---|---|---|---|---|
| miRNA* | OR** | 95% CI (P) | AUC† | 95% CI (P‡) |
| miR_19a | 4.82 | 1.20, 19.33 (0.026) | 0.75 | 0.65, 0.85 (0.41) |
| miR_19b | 5.57 | 1.81, 17.12 (0.003) | 0.77 | 0.68, 0.87 (0.25) |
| miR_345 | 0.13 | 0.03, 0.47 (0.002) | 0.78 | 0.68, 0.87 (0.19) |
| miR_519c_5p | 0.18 | 0.07, 0.49 (0.001) | 0.79 | 0.69, 0.88 (0.18) |
| | VALIDATION COHORT (n = 60) | | | |
| miRNA* | OR** | 95% CI (P) | AUC† | 95% CI (P‡) |
| miR_19a | 9.22 | 2.27, 37.43 (0.002) | 0.85 | 0.75, 0.95 (0.13) |
| miR_19b | 12.67 | 2.72, 58.98 (0.001) | 0.86 | 0.76, 0.96 (0.10) |
| miR_345 | 0.03 | 0.002, 0.37 (0.007) | 0.84 | 0.74, 0.94 (0.09) |
| miR_519c_5p | 0.06 | 0.01, 0.30 (0.001) | 0.88 | 0.80, 0.96 (0.04) |

FIG. 14

| Model* | miRNA | OR | 95% CI (P) | AUC | 95% CI (P) |
|---|---|---|---|---|---|
| 1 | miR_19a | 9.72 | 1.52, 62.10 (0.016) | 0.941 | 0.88, 1.00 (0.007) |
| | miR_345 | 0.01 | 0.00, 0.65 (0.031) | | |
| | miR_519c_5p | 0.05 | 0.01, 0.46 (0.008) | | |
| 2 | miR_19b | 12.49 | 1.64, 94.97 (0.015) | 0.939 | 0.87, 1.00 (0.009) |
| | miR_345 | 0.01 | 0.00, 0.70 (0.034) | | |
| | miR_519c_5p | 0.06 | 0.01, 0.49 (0.009) | | |
| 3 | miR_19a | 1.82 | 0.03, 115.26 (0.780) | 0.939 | 0.87, 1.00 (0.009) |
| | miR_19b | 7.14 | 0.09, 557.08 (0.376) | | |
| | miR_345 | 0.01 | 0.00, 0.70 (0.034) | | |
| | miR_519c_5p | 0.06 | 0.01, 0.50 (0.010) | | |

FIG. 15
A. DISCOVERY COHORT
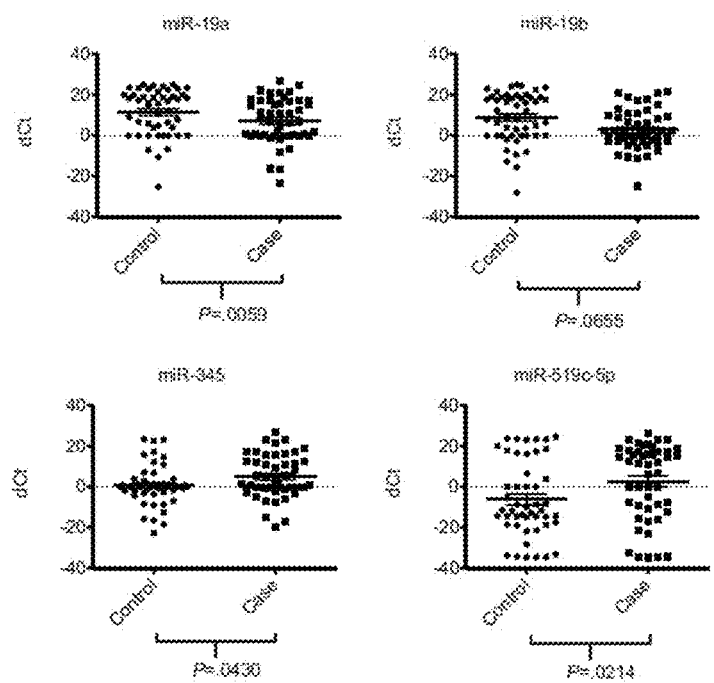
B. VALIDATION COHORT
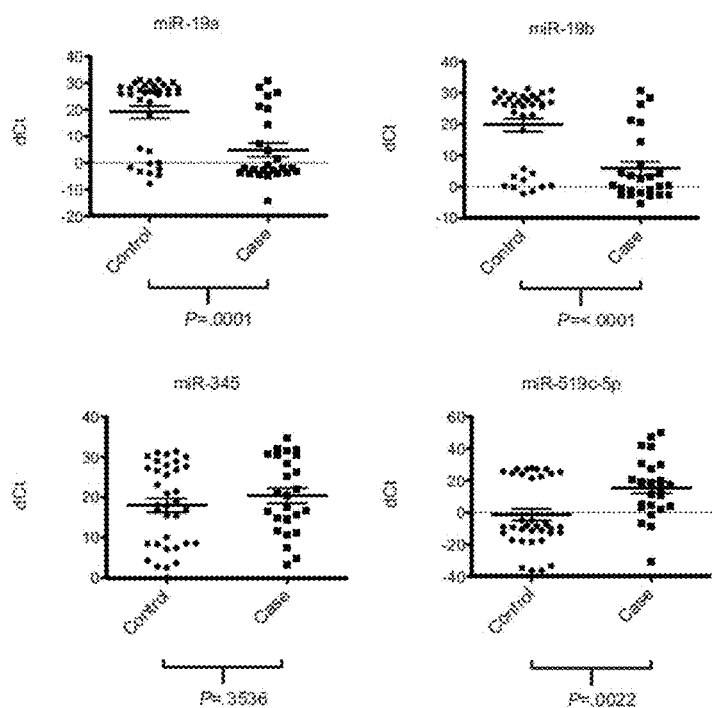

FIG. 17
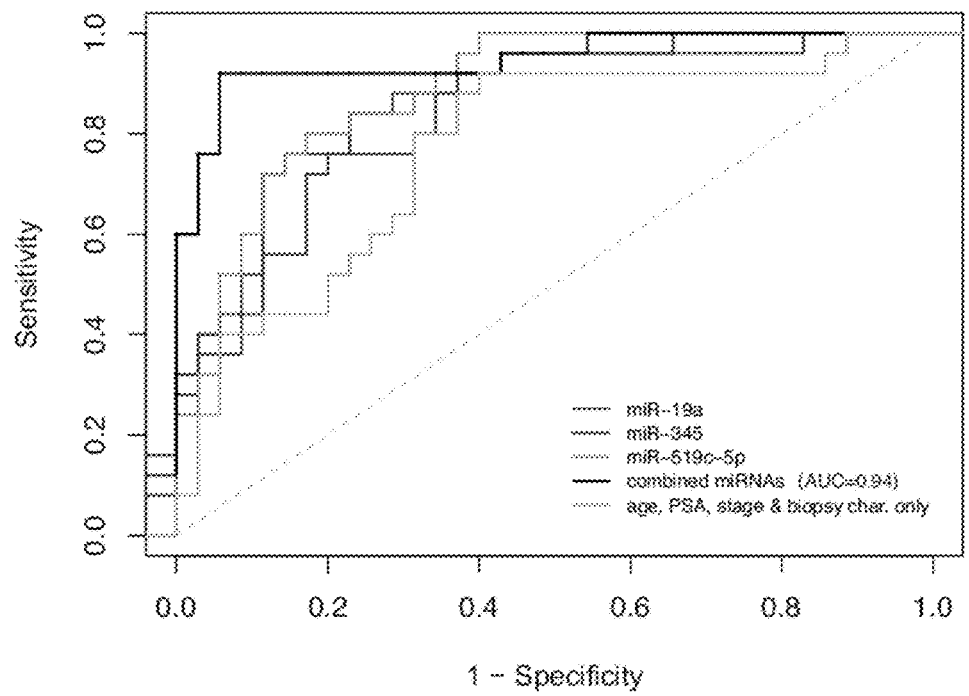
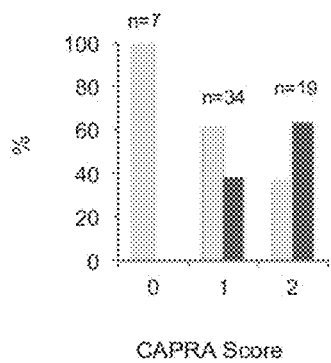
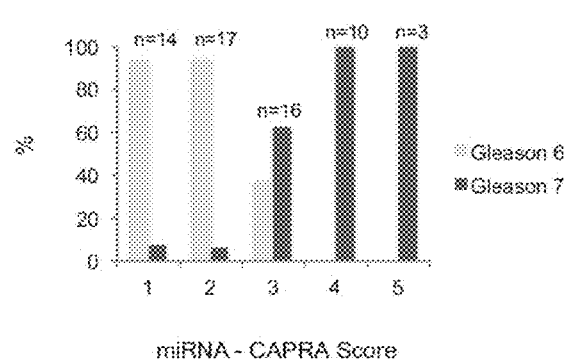

| | | | | | |
|---|---|---|---|---|---|
| hsa/mmu miR-744 | CTCAACTGGTGTCGTGGAGTCGGCAATTCAGTTGAGTGCTGTTA | 209 | ACACTCCAGCTGGGTGCGGGGCTAGGGCTA | 1155 | /56-FAM/TTCAGTTGAGTGCTGTTA/3IABLFQ/ | 2101 |
| hsa/mmu miR-760 | CTCAACTGGTGTCGTGGAGTCGGCAATTCAGTTGAGTCCCCACA | 210 | ACACTCCAGCTGGGCGGCTCTGGGTCTG | 1156 | /56-FAM/TTCAGTTGAGTCCCCACA/3IABLFQ/ | 2102 |
| hsa/mmu miR-7a | CTCAACTGGTGTCGTGGAGTCGGCAATTCAGTTGAGACAACAAA | 211 | ACACTCCAGCTGGGTGGAAGACTAGTGATT | 1157 | /56-FAM/TTCAGTTGAGACAACAAA/3IABLFQ/ | 2103 |
| hsa/mmu miR-873 | CTCAACTGGTGTCGTGGAGTCGGCAATTCAGTTGAGAGGAGACT | 212 | ACACTCCAGCTGGGGCAGGGAACTTGTGAG | 1158 | /56-FAM/TTCAGTTGAGAGGAGACT/3IABLFQ/ | 2104 |
| hsa/mmu miR-874 | CTCAACTGGTGTCGTGGAGTCGGCAATTCAGTTGAGTCGGTCCC | 213 | ACACTCCAGCTGGGCTGCCCTGGCCCGAGG | 1159 | /56-FAM/TTCAGTTGAGTCGGTCCC/3IABLFQ/ | 2105 |
| hsa/mmu miR-875-5p | CTCAACTGGTGTCGTGGAGTCGGCAATTCAGTTGAGCACCTGAT | 214 | ACACTCCAGCTGGGTATACCTCAGTTTAT | 1160 | /56-FAM/TTCAGTTGAGCACCTGAT/3IABLFQ/ | 2106 |
| hsa/mmu miR-877 | CTCAACTGGTGTCGTGGAGTCGGCAATTCAGTTGAGCCCTGCGC | 215 | ACACTCCAGCTGGGTCTTTGGTTATCTAGCT | 1161 | /56-FAM/TTCAGTTGAGCCCTGCGC/3IABLFQ/ | 2107 |
| hsa/mmu miR-9 | CTCAACTGGTGTCGTGGAGTCGGCAATTCAGTTGAGTCATACAG | 216 | ACACTCCAGCTGGGTCTTTGGTTATCTAGCT | 1162 | /56-FAM/TTCAGTTGAGTCATACAG/3IABLFQ/ | 2108 |
| hsa/mmu miR-92b | CTCAACTGGTGTCGTGGAGTCGGCAATTCAGTTGAGGGAGGCCG | 217 | ACACTCCAGCTGGGTATTGCACTCGTCCCG | 1163 | /56-FAM/TTCAGTTGAGGGAGGCCG/3IABLFQ/ | 2109 |
| hsa/mmu miR-93 | CTCAACTGGTGTCGTGGAGTCGGCAATTCAGTTGAGCTACCTGC | 218 | ACACTCCAGCTGGGCAAAGTGCTGTTCGTGC | 1164 | /56-FAM/TTCAGTTGAGCTACCTGC/3IABLFQ/ | 2110 |
| hsa/mmu miR-95 | CTCAACTGGTGTCGTGGAGTCGGCAATTCAGTTGAGAGCAAAAA | 219 | ACACTCCAGCTGGGTTTGGCACTAGCACATT | 1165 | /56-FAM/TTCAGTTGAGAGCAAAAA/3IABLFQ/ | 2111 |
| hsa/mmu miR-98 | CTCAACTGGTGTCGTGGAGTCGGCAATTCAGTTGAGAACAATAC | 220 | ACACTCCAGCTGGGTGAGGTAGTAAGTTGT | 1166 | /56-FAM/TTCAGTTGAGAACAATAC/3IABLFQ/ | 2112 |
| hsa/mmu miR-99a | CTCAACTGGTGTCGTGGAGTCGGCAATTCAGTTGAGCACAAGAT | 221 | ACACTCCAGCTGGGAACCCGTAGATCCGAT | 1167 | /56-FAM/TTCAGTTGAGCACAAGAT/3IABLFQ/ | 2113 |
| hsa/mmu miR-99b | CTCAACTGGTGTCGTGGAGTCGGCAATTCAGTTGAGCGCAAGGT | 222 | ACACTCCAGCTGGGCACCCGTAGAACCGAC | 1168 | /56-FAM/TTCAGTTGAGCGCAAGGT/3IABLFQ/ | 2114 |

| Name | Sequence 1 | # | Sequence 2 | # | Probe |
|---|---|---|---|---|---|
| hsa-miR-770-5p | CTCAACTGGTGTCGTGGAGTCGGCAATTCAGTTGAGTGAGCCCTG | 642 | ACACTCCAGCTGGGTCCAGTACCACGTGTCA | 1588 | /56-FAM/TTCAGTTGAGTGGCCCTG/3IABLFQ/ |
| hsa-miR-802 | CTCAACTGGTGTCGTGGAGTCGGCAATTCAGTTCAGTTGAGACAAGGAT | 643 | ACACTCCAGCTGGGTCCAGTAAACAAAGATTCAT | 1589 | /56-FAM/TTCAGTTGAGACAAGGAT/3IABLFQ/ |
| hsa-miR-875-3p | CTCAACTGGTGTCGTGGAGTCGGCAATTCAGTTGAGCACAACCT | 644 | ACACTCCAGCTGGGCCTGGAAACACTGAG | 1590 | /56-FAM/TTCAGTTGAGCACAACCT/3IABLFQ/ |
| hsa-miR-876-3p | CTCAACTGGTGTCGTGGAGTCGGCAATTCAGTTGAGTGAATTAC | 645 | ACACTCCAGCTGGGTGGTCGTTTACAAAGT | 1591 | /56-FAM/TTCAGTTGAGTGAATTAC/3IABLFQ/ |
| hsa-miR-876-5p | CTCAACTGGTGTCGTGGAGTCGGCAATTCAGTTGAGTGGTGATT | 646 | ACACTCCAGCTGGGTGGTGATTTCTTTGTGAA | 1592 | /56-FAM/TTCAGTTGAGTGGTGATT/3IABLFQ/ |
| hsa-miR-885-3p | CTCAACTGGTGTCGTGGAGTCGGCAATTCAGTTGAGTATCCACT | 647 | ACACTCCAGCTGGGTCAGGCAGGTATCCACT | 1593 | /56-FAM/TTCAGTTGAGTATCCACT/3IABLFQ/ |
| hsa-miR-885-5p | CTCAACTGGTGTCGTGGAGTCGGCAATTCAGTTGAGAGAGGCAG | 648 | ACACTCCAGCTGGGTCCATTACACTACCCT | 1594 | /56-FAM/TTCAGTTGAGAGAGGCAG/3IABLFQ/ |
| hsa-miR-886-3p | CTCAACTGGTGTCGTGGAGTCGGCAATTCAGTTGAGAAGGGTCA | 649 | ACACTCCAGCTGGGCGCGGTGCTTACTG | 1595 | /56-FAM/TTCAGTTGAGAAGGGTCA/3IABLFQ/ |
| hsa-miR-886-5p | CTCAACTGGTGTCGTGGAGTCGGCAATTCAGTTGAGCCGCTTGA | 650 | ACACTCCAGCTGGGCGGGTCGGAGTTAGCTC | 1596 | /56-FAM/TTCAGTTGAGCCGCTTGA/3IABLFQ/ |
| hsa-miR-887 | CTCAACTGGTGTCGTGGAGTCGGCAATTCAGTTGAGCCCTCGGGA | 651 | ACACTCCAGCTGGGGTGAACGGCGCCAATC | 1597 | /56-FAM/TTCAGTTGAGCCCTCGGGA/3IABLFQ/ |
| hsa-miR-888 | CTCAACTGGTGTCGTGGAGTCGGCAATTCAGTTGAGTGACTGAC | 652 | ACACTCCAGCTGGGTACTCAAAAAGCTGT | 1598 | /56-FAM/TTCAGTTGAGTGACTGAC/3IABLFQ/ |
| hsa-miR-889 | CTCAACTGGTGTCGTGGAGTCGGCAATTCAGTTGAGACAATGGT | 653 | ACACTCCAGCTGGGTTAATATCGGACAAC | 1599 | /56-FAM/TTCAGTTGAGACAATGGT/3IABLFQ/ |
| hsa-miR-890 | CTCAACTGGTGTCGTGGAGTCGGCAATTCAGTTGAGCAACTGAT | 654 | ACACTCCAGCTGGGTACTTGGAAAGGCAT | 1600 | /56-FAM/TTCAGTTGAGCAACTGAT/3IABLFQ/ |
| hsa-miR-891a | CTCAACTGGTGTCGTGGAGTCGGCAATTCAGTTGAGTCAGTGGC | 655 | ACACTCCAGCTGGGTGCAACGAACCTGAGC | 1601 | /56-FAM/TTCAGTTGAGTCAGTGGC/3IABLFQ/ |
| hsa-miR-891b | CTCAACTGGTGTCGTGGAGTCGGCAATTCAGTTGAGTCAATGAC | 656 | ACACTCCAGCTGGGTGCAACTTACCTGAGT | 1602 | /56-FAM/TTCAGTTGAGTCAATGAC/3IABLFQ/ |
| hsa-miR-892a | CTCAACTGGTGTCGTGGAGTCGGCAATTCAGTTGAGCTACGCAG | 657 | ACACTCCAGCTGGGCCACTGTGTCCTTCT | 1603 | /56-FAM/TTCAGTTGAGCTACGCAG/3IABLFQ/ |
| hsa-miR-892b | CTCAACTGGTGTCGTGGAGTCGGCAATTCAGTTGAGTCACCCA | 658 | ACACTCCAGCTGGGCACTGGCCTCCTTCTG | 1604 | /56-FAM/TTCAGTTGAGTCACCCA/3IABLFQ/ |
| hsa-miR-920 | CTCAACTGGTGTCGTGGAGTCGGCAATTCAGTTGAGTACTGCTT | 659 | ACACTCCAGCTGGGGGGGAGCTGTGAA | 1605 | /56-FAM/TTCAGTTGAGTACTGCTT/3IABLFQ/ |
| hsa-miR-921 | CTCAACTGGTGTCGTGGAGTCGGCAATTCAGTTGAGGAATCCTG | 660 | ACACTCCAGCTGGGCTAGTGAGGGACAAGAACCA | 1606 | /56-FAM/TTCAGTTGAGGAATCCTG/3IABLFQ/ |
| hsa-miR-922 | CTCAACTGGTGTCGTGGAGTCGGCAATTCAGTTGAGGACGTAGT | 661 | ACACTCCAGCTGGGCAGCAGCAGAATAGGAC | 1607 | /56-FAM/TTCAGTTGAGGACGTAGT/3IABLFQ/ |
| hsa-miR-923 | CTCAACTGGTGTCGTGGAGTCGGCAATTCAGTTGAGAGTTCTT | 662 | ACACTCCAGCTGGGGTACGCGGAGGAAAA | 1608 | /56-FAM/TTCAGTTGAGAGTTCTT/3IABLFQ/ |
| hsa-miR-924 | CTCAACTGGTGTCGTGGAGTCGGCAATTCAGTTGAGGCAAGACA | 663 | ACACTCCAGCTGGGAGAGTCTTGTGATG | 1609 | /56-FAM/TTCAGTTGAGGCAAGACA/3IABLFQ/ |
| hsa-miR-92b | CTCAACTGGTGTCGTGGAGTCGGCAATTCAGTTGAGACAGGCCG | 664 | ACACTCCAGCTGGGTATTGCACTTGTCCCG | 1610 | /56-FAM/TTCAGTTGAGACAGGCCG/3IABLFQ/ |
| hsa-miR-933 | CTCAACTGGTGTCGTGGAGTCGGCAATTCAGTTGAGGGGAGAGG | 665 | ACACTCCAGCTGGGTGTGCCAGGAGACC | 1611 | /56-FAM/TTCAGTTGAGGGGAGAGG/3IABLFQ/ |
| hsa-miR-934 | CTCAACTGGTGTCGTGGAGTCGGCAATTCAGTTGAGCCAGTGTC | 666 | ACACTCCAGCTGGGTGTCTACTACTGGAGA | 1612 | /56-FAM/TTCAGTTGAGCCAGTGTC/3IABLFQ/ |
| hsa-miR-935 | CTCAACTGGTGTCGTGGAGTCGGCAATTCAGTTGAGGCGGTAGC | 667 | ACACTCCAGCTGGGCCAGTTACCGCTTCCGC | 1613 | /56-FAM/TTCAGTTGAGGCGGTAGC/3IABLFQ/ |
| hsa-miR-936 | CTCAACTGGTGTCGTGGAGTCGGCAATTCAGTTGAGCTGCGATT | 668 | ACACTCCAGCTGGGACAGTAGAGGGAGGAA | 1614 | /56-FAM/TTCAGTTGAGCTGCGATT/3IABLFQ/ |
| hsa-miR-937 | CTCAACTGGTGTCGTGGAGTCGGCAATTCAGTTGAGACTGGGTT | 669 | ACACTCCAGCTGGGATCCGCGCTCTGACTC | 1615 | /56-FAM/TTCAGTTGAGACTGGGTT/3IABLFQ/ |
| hsa-miR-938 | CTCAACTGGTGTCGTGGAGTCGGCAATTCAGTTGAGAACGTGAA | 670 | ACACTCCAGCTGGGTGCCCTTAAAGCTGAA | 1616 | /56-FAM/TTCAGTTGAGAACGTGAA/3IABLFQ/ |
| hsa-miR-939 | CTCAACTGGTGTCGTGGAGTCGGCAATTCAGTTGAGCACCCCA | 671 | ACACTCCAGCTGGGTGGGGAGCTGAGGCTCTG | 1617 | /56-FAM/TTCAGTTGAGCACCCCA/3IABLFQ/ |
| hsa-miR-940 | CTCAACTGGTGTCGTGGAGTCGGCAATTCAGTTGAGGGGGAGCG | 672 | ACACTCCAGCTGGGAAGGCAGGGGCCCCCG | 1618 | /56-FAM/TTCAGTTGAGGGGGAGCG/3IABLFQ/ |
| hsa-miR-941 | CTCAACTGGTGTCGTGGAGTCGGCAATTCAGTTGAGCACATGT | 673 | ACACTCCAGCTGGGCACCCGGCTGTGTGCAC | 1619 | /56-FAM/TTCAGTTGAGCACATGT/3IABLFQ/ |
| hsa-miR-942 | CTCAACTGGTGTCGTGGAGTCGGCAATTCAGTTGAGCACATGGC | 674 | ACACTCCAGCTGGGTCTTCTCTGTTTTGGC | 1620 | /56-FAM/TTCAGTTGAGCACATGGC/3IABLFQ/ |
| hsa-miR-943 | CTCAACTGGTGTCGTGGAGTCGGCAATTCAGTTGAGCTGGAGGA | 675 | ACACTCCAGCTGGGCTGACTGTTGCCGTC | 1621 | /56-FAM/TTCAGTTGAGCTGGAGGA/3IABLFQ/ |
| hsa-miR-944 | CTCAACTGGTGTCGTGGAGTCGGCAATTCAGTTGAGCTCATCCG | 676 | ACACTCCAGCTGGGAAATATTGTACATCG | 1622 | /56-FAM/TTCAGTTGAGCTCATCCG/3IABLFQ/ |
| hsa-miR-95 | CTCAACTGGTGTCGTGGAGTCGGCAATTCAGTTGAGTGCTCAAT | 677 | ACACTCCAGCTGGGTTCAACGGGTATTTAT | 1623 | /56-FAM/TTCAGTTGAGTGCTCAAT/3IABLFQ/ |

| Name | Sequence | SEQ ID | Probe | SEQ ID |
|---|---|---|---|---|
| mmu miR-879 | CTCAACTGGTGTCGTGGAGTCGGCAATTCAGTTGAGGGCTTAGA | 938 | ACACTCCAGCTGGGAGACGGCTTATAGCTTC | 1884 | /56-FAM/TTCAGTTGAGGGCTTAGA/3IABLFQ/ | 2830 |
| mmu miR-880 | CTCAACTGGTGTCGTGGAGTCGGCAATTCAGTTGAGTCTACTCA | 939 | ACACTCCAGCTGGGTACTCCATCCTCTCTG | 1885 | /56-FAM/TTCAGTTGAGTCTACTCA/3IABLFQ/ | 2831 |
| mmu miR-881 | CTCAACTGGTGTCGTGGAGTCGGCAATTCAGTTGAGTCTATTCA | 940 | ACACTCCAGCTGGGAACTGTGTCTTTTCTG | 1886 | /56-FAM/TTCAGTTGAGTCTATTCA/3IABLFQ/ | 2832 |
| mmu miR-882 | CTCAACTGGTGTCGTGGAGTCGGCAATTCAGTTGAGACTAATGC | 941 | ACACTCCAGCTGGGAGGAGAGAGTTAGCUGC | 1887 | /56-FAM/TTCAGTTGAGACTAATGC/3IABLFQ/ | 2833 |
| mmu miR-883a-3p | CTCAACTGGTGTCGTGGAGTCGGCAATTCAGTTGAGATACTGAG | 942 | ACACTCCAGCTGGGTAACTGCAACAGCTCT | 1888 | /56-FAM/TTCAGTTGAGATACTGAG/3IABLFQ/ | 2834 |
| mmu miR-883a-5p | CTCAACTGGTGTCGTGGAGTCGGCAATTCAGTTGAGGTAACTGC | 943 | ACACTCCAGCTGGGTGCTGAGAGAAGTAGC | 1889 | /56-FAM/TTCAGTTGAGGTAACTGC/3IABLFQ/ | 2835 |
| mmu miR-883b-3p | CTCAACTGGTGTCGTGGAGTCGGCAATTCAGTTGAGATACTGAG | 944 | ACACTCCAGCTGGGTAACTGCAACATCTCT | 1890 | /56-FAM/TTCAGTTGAGATACTGAG/3IABLFQ/ | 2836 |
| mmu miR-883b-5p | CTCAACTGGTGTCGTGGAGTCGGCAATTCAGTTGAGTGACTGCT | 945 | ACACTCCAGCTGGGTACTGAGAATGGGTAG | 1891 | /56-FAM/TTCAGTTGAGTGACTGCT/3IABLFQ/ | 2837 |
| mmu miR-92a | CTCAACTGGTGTCGTGGAGTCGGCAATTCAGTTGAGCAGGCCGG | 946 | ACACTCCAGCTGGGTATTGCACTTGTCCC | 1892 | /56-FAM/TTCAGTTGAGCAGGCCGG/3IABLFQ/ | 2838 |

METHODS AND SYSTEMS FOR
DETERMINING A LIKELIHOOD OF
ADVERSE PROSTATE CANCER
PATHOLOGY

CROSS-REFERENCE TO RELATED APPLICATIONS

This application is a continuation of international application serial no. PCT/US2013/068126, filed Nov. 1, 2013, which application claims priority to the filing date of U.S. Provisional Application Ser. No. 61/721,699 filed Nov. 2, 2012, the disclosure of which is herein incorporated by reference in its entirety.

STATEMENT REGARDING FEDERALLY SPONSORED RESEARCH

This invention was made with government support under Grant No. CA161615 awarded by the National Institutes of Health. The government has certain rights in the invention.

INTRODUCTION

Prostate cancer is the fifth most common malignancy in the world, with over 200,000 new cases diagnosed in North America annually. While screening has decreased prostate cancer mortality rates, it has done so at the risk of detecting early stage/grade prostate cancer that might not affect a patient's life if untreated. Treating those with low risk disease results in unnecessary morbidities associated with radical interventions such as surgery or radiation.

Active surveillance (AS) is a strategy developed to reduce the treatment of patients with low risk prostate cancer. Such patients are often monitored with physical exams, selective imaging, PSA assessments, and/or repeat biopsies. Treatment is then offered to those with signs of progression. Although AS is a viable option for men with low-risk prostate cancer, there are considerable misclassification rates when identifying candidates for AS. Accordingly, nomograms have been developed to predict post-surgical pathology in low-risk patients utilizing clinical characteristics such as age, PSA, and stage. However, existing approaches demonstrate a low accuracy rate, complicating decision-making. Further, due to the limitations of PSA as a surrogate for disease progression and the significant concerns about biopsy sampling errors, both patients and clinicians worry that delayed treatment compromises the ability to cure disease.

SUMMARY

The present disclosure provides methods that find use in determining a likelihood of adverse prostate cancer pathology in a subject. The methods generally involve detection of one or more diagnostic microRNAs (miRNAs), such as mir-19a, mir-19b, mir-519c-5p, and/or mir-345. The detection of one or more (e.g., a combination) of such diagnostic miRNAs can be used to determine a likelihood of adverse prostate cancer pathology in a subject. The methods of the present disclosure also find use in facilitating treatment decisions for a subject. Also provided are devices, systems, and kits that may be used in practicing methods of the present disclosure.

The present disclosure provides methods of determining a likelihood of adverse prostate cancer pathology in a subject, the methods including determining an amount of at least one diagnostic miRNA in a biological sample from the subject, comparing the amount of the at least one diagnostic miRNA with a reference amount, and generating a report indicating a likelihood of adverse prostate cancer pathology in the subject based on results of said comparing the amount of the at least one diagnostic miRNA with the reference amount. The biological sample used in the methods of the present disclosure can be blood or blood product, e.g., serum or plasma. The methods may optionally include obtaining the biological sample from the subject.

The means of determining an amount of a diagnostic miRNA in a biological sample may vary. In some aspects, determining the amount of a diagnostic miRNA involves performing quantitative real-time PCR, such as multiplexed quantitative real-time PCR. The amount of the diagnostic miRNA may be compared to a reference amount calculated in a variety of different ways. In some aspects, the reference amount is a control amount of the diagnostic miRNA. In other aspects, the reference amount may be calculated from cycle threshold (Ct) values of a plurality of reference miRNAs from the biological sample, such as by computing a median Ct value from the plurality. Reference miRNAs of interest include, but are not limited to, mir-17, mir-20a, mir-92a, mir-106a, mir-93, mir-25, let-7b, mir-24, mir-939, mir-1234, mir-522, mir-525-5p, mir-660, mir-941, mir-1274a, mir-1274b, mir-302f, mir-34c-3p, mir-663, mir-197, mir-223, mir-297, mir-346, mir-484, mir-486, mir-584, mir-638, mir-629, mir-720, mir-942, mir-1208, and mir-1243. Further, in some aspects a reference amount may be calculated based upon a biomolecule that is not a miRNA, such as a polypeptide (e.g., a protein or peptide), long non-coding RNA molecule, small RNA(s), spiked-in RNAs, and the like.

The methods may optionally indicate a likelihood of adverse prostate cancer pathology in a subject by taking into account one or more additional risk factors. Risk factors of interest include, but are not limited to, factors that may be assessed without biopsying the subject, such as the subject's age, prostate-specific antigen (PSA) level, and/or clinical stage. In certain aspects, the methods include measuring the subject's PSA level and/or determining the subject's clinical stage. Risk factors of interest further include, but are not limited to, factors that may be assessed from a biopsy (e.g., a biopsy of the subject's prostate), including the subject's Gleason score, the percentage of biopsy cores positive, the fraction of the biopsy that is positive, or any combination thereof. In certain aspects, the methods include biopsying the subject's prostate.

The methods of the present disclosure can include selecting a therapy for the subject based on the likelihood of adverse prostate cancer pathology, where in some embodiments the treatment recommendation is active surveillance, watchful waiting, or a similar non-invasive approach. The methods of the present disclosure can include administering a therapy for the subject based on the likelihood of adverse prostate cancer pathology. Where the subject is undergoing therapy, the methods of the present disclosure can include modifying therapy for the subject based on the results of the assay(s).

The methods of the present disclosure can involve inputting the amount of one or more diagnostic miRNAs into a computer programmed to execute an algorithm to perform the comparing step, wherein said inputting generates a result for a report. The report can be displayed to an output device, e.g., at a location remote to the computer.

The present disclosure also provides devices for determining a likelihood of adverse prostate cancer pathology in a subject. The devices include an analyzing unit comprising a detection agent for one or more diagnostic miRNAs, where the analyzing unit is configured for determining an amount of the diagnostic miRNA(s) in a biological sample detected by the detection agent; and an evaluation unit comprising a processor programmed to compare the determined amount(s) obtained from the analyzing unit with a reference amount; and calculate a likelihood of adverse prostate cancer pathology in the subject, based on results of the comparing the determined amount(s) obtained from the analyzing unit with the reference amount. In certain aspects, the processor of the evaluation unit is programmed to calculate a likelihood of adverse prostate cancer pathology in the subject based on one or more additional risk factors, such as the subject's age, PSA level, clinical stage, Gleason score, percentage of biopsy cores positive, the fraction of the biopsy that is positive, and the like. The device may optionally include a display comprising a user interface configured to receive user input (e.g., input as to the subject's age, PSA level, and the like) and provide the input to the processor.

Also provided by the present disclosure are kits, such as kits that include a detection agent for one or more diagnostic miRNA molecules, and a device for determining a likelihood of adverse prostate cancer pathology in a subject (e.g., a device as described above).

The present disclosure also provides computer systems for determining a likelihood of adverse prostate cancer pathology in a subject. The computer systems include a processor and memory operably coupled to the processor, where the memory programs the processor to receive assay data including an amount of at least one diagnostic miRNA in a biological sample from a subject; compare the amount received with a reference amount; and calculate a likelihood of adverse prostate cancer pathology in the subject, based on results of said comparing the determined amounts obtained from the analyzing unit with the reference amount. In certain aspects, the system calculates a likelihood of adverse prostate cancer pathology in the subject based on one or more additional risk factors, such as the subject's age, PSA level, etc.

These and other features will be apparent to the ordinarily skilled artisan upon reviewing the present disclosure.

BRIEF DESCRIPTION OF THE DRAWINGS

The invention may be best understood from the following detailed description when read in conjunction with the accompanying drawings. Included in the drawings are the following figures:

FIG. 1 is a schematic of a design of a first study. Patients met the UCSF low-risk criteria for AS including biopsy Gleason 2-6 (no pattern 4 or 5), PSA less than 10 ng/ml, less than 33% of biopsy cores involved, less than 50% involvement in any single core, and clinical T1-T2 stage disease. All selected patients chose to undergo immediate radical prostatectomy. A Gleason score of 7 of higher was used to define adverse prostate cancer pathology. The discovery cohort consisted of 48 patients with a post-surgical specimen Gleason score ≥7 (case group) and 48 patients with a post-surgical specimen Gleason score of 6 (control group). A validation cohort consisted of 46 patients in case and 50 patients in control group.

FIG. 2 is a table listing patient characteristics of the discovery and validation cohorts. In the discovery cohort, there were no statistically significant differences in race, PSA, or clinical stage between the case and control groups, though the case group did have a significantly higher age than the control group (p=0.009). Similar to the discovery cohort, there were no statistically significant differences in race, PSA, or clinical stage between cases and controls in the validation cohort, though the case group was significantly older than the control group (p=0.002).

FIG. 3 is a table listing miRNAs for which detectable Ct values were demonstrated in at least 30% of the patients according to multiplex qRT-PCR on a microfluidics platform. Detectable Ct values were demonstrated for 36 of the 672 miRNAs evaluated in serum of 96 patients with pre-surgical low risk disease (PSA<10, Gleason<7 with no 4+2, clinical stage <T3), but chose surgery over AS (see FIGS. 1-2).

FIG. 8, Panels A-B show CAPRA and modified CAPRA scores by case status in the validation cohort. Panel A: distribution of CAPRA scores for patients in the validation cohort. Panel B: modified CAPRA scores were produced by adding one point to the score for each positive miRNA (considering only mir-19a, mir-19b, and mir-519c-5p), where positivity is detection of a value exceeding the median detectable value. The resulting score (miRNA+CAPRA) displayed a significant increasing linear trend (p<0.001) in outcome risk, with 100% of the 12 individuals scored at the highest level (5) classified as cases.

FIG. 12 is a table showing miRNAs consistently detected in the serum from the discovery cohort.

FIG. 13 is a table showing summaries of logistic regression models for individual miRNAs in the discovery and validation cohorts accounting for age, PSA, stage and biopsy characteristics. *miRNAs were represented in models as binary indicators, with cut-offs selected using a classification tree. **Estimated odds ratio from a logistic regression also controlling for age, PSA, stage and degree of biopsy involvement. † Estimated area under the ROC curve from a logistic regression also controlling for age, PSA, stage and degree of biopsy involvement. ‡ P-value comparing AUC for model including for miRNA, to model including only age, PSA, stage and degree of biopsy involvement.

FIG. 14 is a table showing summaries of logistic regression models for different combinations of miRNAs in validation cohort accounting for age, PSA, stage and biopsy characteristics.

FIG. 15 shows distribution plots for serum miR-19b, miR-19a, miR-345, and miR-519c-5p delta Ct values in case versus control for a) discovery cohort, b) validation cohort. Delta Ct represents difference between Ct of individual miRNA and median Ct value among detected miRNAs within each patient. Horizontal bars represent mean+/−SEM.

FIG. 17 shows prediction models for miRNAs. Panel A: ROC curves for age, PSA, and stage plus/minus individual miRNAs or combination of all 3 miRNAs; Panel B: Percentage of patients with either Gleason 6 (light grey) or Gleason 7 (dark grey) post-surgery relative to pre-surgery CAPRA score; Panel C: Same as Panel B, but with addition of miRNAs. A value of 1 is given for each positive miRNA and added to CAPRA score. CAPRA nomogram combines the following variables: Age at diagnosis, PSA at diagnosis, Gleason score of pre-surgical biopsy, Clinical stage, and Percent of involved biopsies.

FIGS. 19A-C are tables listing stem-loop primers, forward primers, and Taqman probes.

DETAILED DESCRIPTION

Figure 4:
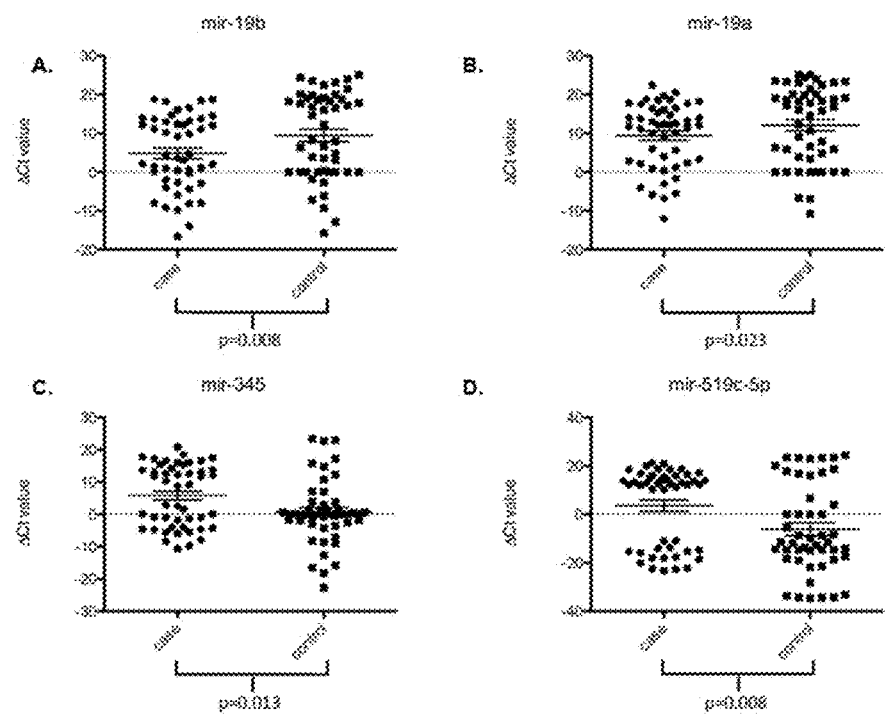
FIG. 4, Panels A-D depict the four detected miRNAs that demonstrated differences in serum levels between the cases and controls. Mir-19b (Panel A) and mir-19a (Panel B) had significantly lower ΔCt values in the case group when compared to the controls (p=0.008 and p=0.023, respectively), showing higher serum expression in the case group. Conversely, mir-345 (Panel C) and mir-519c-5p (Panel D) had significantly higher ΔCt values in the case group when compared to the controls (p=0.013 and p=0.008, respectively), showing lower serum expression in the case group.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a biological sample" includes a plurality of such biological samples and reference to "the processor" includes reference to one or more processors, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Definitions

The term "prostate cancer" is known in the art, and refers to a proliferative lesion or abnormality of the prostate. Accordingly, the term encompasses benign lesions, premalignant lesions, malignant lesions as well as solid tumors and metastatic disease (both locally metastatic and more widely metastatic).

The terms "staging prostate cancer" and "clinical stage" are used to differentiate between various stages of prostate cancer. The general classification of prostate tumor stages is well-known to the skilled artisan. In brief, the most commonly used staging method is the Tumor, Nodes, Metastasis (TNM) system, which recognizes four stages of local tumor growth, from T1 (incidental) to T4 (invasion of neighboring organs). Each stage describes the state of pathological development of the tumor. T1 represents an 'incidental' state, where the tumor is detected by chance following transurethral resection or by biopsy following PSA testing. At this stage, the tumor will be undetectable by palpation (DRE) or ultrasound, but may be diagnosed by the method of the present invention. T4 represents advanced disease, where the tumor has invaded neighboring organs. The nodal stage (N0-N1) and the metastatic stage (M0-M1C) reflect the clinical spread of the disease to lymph nodes and distant sites (metastasis), respectively.

Grading systems can assess the degree of cell anaplasia (variation in size, shape and staining properties) and differentiation (how well differentiated the cells are) in the tumor. The Gleason grading system is based on the extent to which the tumor cells are arranged into recognizably glandular structures and the level of cell differentiation. The Gleason system identifies more than five levels of increasing disease aggressiveness, with Grade 1 being the least aggressive and over Grade 5 being the most aggressive cancer. The Gleason system is described in, e.g., Gleason, D. F. (1977) *Urologic Pathology: The Prostate*. Philadelphia: Lea and Febiger. pp. 171-198; the disclosure of which is incorporated herein by reference.

In certain embodiments of the method of the present invention, it is differentiated between high risk, an intermediate risk and a low risk. A subject at "low risk" is generally a subject suffering from prostate cancer with a Gleason score of 6 or lower than 6. "Low risk" subjects may include those with Gleason 2-6 (no pattern 4 or 5), PSA less than 10 ng/ml, less than 33% of biopsy cores involved, less than 50% involvement in any single core, and clinical T1-T2 stage disease. A subject being at "intermediate risk" in the context of the method of the present invention relates to subject suffering from prostate cancer with a Gleason score of 7. A Gleason score of 7 is associated with an increased risk of disease-specific mortality, and suggests a risk of clinical progression. A subject being at "high risk" in the context of the method of the present invention relates to subject suffering from prostate cancer with a Gleason score of 8 or larger than 8.

The terms "adverse pathology" with reference to a subject having, at risk of having or suspected of having prostate cancer and "adverse prostate cancer pathology" denote a Gleason score of 7 or higher and/or any pattern 4 or higher. Such a Gleason score is associated with an increased risk of prostate cancer-specific mortality, as described in, e.g., Albertsen P C, et al. (2005) *JAMA* 293:2095-2101; the disclosure of which is incorporated herein by reference.

A "biomarker" or "marker" as used herein generally refers to an organic biomolecule (e.g., a microRNA) which is differentially present in a sample taken from a subject of one phenotypic status (e.g., having a disease) as compared with another phenotypic status (e.g., not having the disease or having a different disease). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. As such, biomarkers can find use as markers for, for example, disease (diagnostics), therapeutic effectiveness of a drug (theranostics), and the like. Biomarkers are thus analytes in assays that facilitate diagnosis, theranostics, and the like.

The terms "microRNA" and "miRNA" are used in accord with their ordinary usage in the art. Generally speaking, miRNA are short (e.g., about 18-24 nucleotides in length), non-coding RNAs, which regulate gene expression post-transcriptionally by destabilizing messenger RNAs (mRNA) and/or inhibiting their translation. Canonical miRNAs derive from longer polymerase II transcripts, called pri-miRNAs. A complex consisting of the proteins DGCR8 and Drosha process the pri-miRNAs to pre-miRNAs, which are then exported to the cytoplasm and cleaved by the protein Dicer to mature miRNAs. Exceptions to this processing include non-canonical miRNAs that bypass DGCR8/Drosha, while still being processed by Dicer. Knockout models of Dgcr8 and Dicer have been developed that remove only canonical miRNAs or both canonical and non-canonical miRNAs, respectively.

The term "diagnostic miRNA" refers to mir-19a, mir-19b, mir-519c-5p, and/or miR-345. A diagnostic miRNA is a biomarker. Accordingly, a diagnostic miRNA may be differentially present in a sample taken from a subject of one phenotypic status (e.g., having prostate cancer) as compared with another phenotypic status (e.g., not having the disease or having a different disease). Further, a diagnostic miRNA may be differentially present in a sample taken from a subject having a certain risk level of a disease (e.g., a patient with low risk prostate cancer, and/or a patient without adverse prostate cancer pathology) as compared with another phenotypic status (e.g., a patient with intermediate- or high-risk prostate cancer, and/or a patient with adverse prostate cancer pathology).

In contrast, term "reference miRNA" is used to refer to a miRNA present in a sample that is not a diagnostic miRNA. As such, one or more reference miRNA(s) may be used to establish a reference amount against which an amount of a diagnostic miRNA may be compared, as described more fully herein. Examples of reference miRNAs of interest include, but are not limited to, mir-17, mir-20a, mir-92a, mir-106a, mir-93, mir-25, let-7b, mir-24, mir-939, mir-1234, mir-522, mir-525-5p, mir-660, mir-941, mir-1274a, mir-1274b, mir-302f, mir-34c-3p, mir-663, mir-197, mir-223, mir-297, mir-346, mir-484, mir-486, mir-584, mir-638, mir-629, mir-720, mir-942, mir-1208, and mir-1243.

The terms "individual," "subject," and "patient," used interchangeably herein, refer to a male human.

The term "healthy individual" in the context of the methods of the present disclosure refers to an individual who is unaffected by a detectable illness, particularly prostate cancer.

A "biological sample" encompasses a variety of sample types obtained from an individual. The definition encompasses biological fluids (e.g., blood (including blood fractions (e.g., serum, plasma)); and other liquid samples of biological origin (e.g., saliva, urine, bile fluid), as well as solid tissue samples in the form of a liver biopsy specimen. "Blood sample" refers to a biological sample, which is obtained from blood of a subject, and includes whole blood and blood fractions (e.g., plasma or serum) suitable for analysis in the present methods. In general, separation of cellular components and non-cellular components in a blood sample (e.g., by centrifugation) without coagulation provides a blood plasma sample, while such separation of coagulated (clotted) blood provides a blood serum sample. Examples of biological samples of blood include peripheral blood or samples derived from peripheral blood. The definition also includes samples that have been manipulated after their procurement, such as by treatment with reagents, solubilization, or enrichment for certain components, such as one or more polypeptides to be assayed. For example, a biological sample (e.g., blood) can be enriched for a fraction containing an analyte(s) of interest.

"Isolated" refers to an entity of interest that is in an environment different from that in which the compound may naturally occur. "Isolated" is meant to include compounds that are within samples that are substantially enriched for the compound of interest and/or in which the compound of interest is partially or substantially purified.

By "purified" is meant a compound of interest (e.g., an RNA, DNA or polypeptide) has been separated from components that accompany it in nature. "Purified" can also be used to refer to a compound of interest separated from components that can accompany it during manufacture (e.g., in chemical synthesis). In some embodiments, a compound is substantially pure when it is at least 50% to 60%, by weight, free from organic molecules with which it is naturally associated or with which it is associated during manufacture. In some embodiments, the preparation is at least 75%, at least 90%, at least 95%, or at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample that contains the compound. A substantially pure compound can also be obtained by recombinant or chemical synthetic production. Purity can be measured by any appropriate method, e.g., chromatography, mass spectroscopy, high performance liquid chromatography analysis, etc.

As used herein, the terms "determining", "assessing", "assaying", "measuring" and "detecting" refer to both quantitative and semi-quantitative determinations and as such, the term "determining" is used interchangeably herein with "assaying," "measuring," and the like. Where a quantitative determination is intended, the phrase "determining an amount" of an analyte and the like is used. Where either a quantitative and semi-quantitative determination is intended, the phrase "determining a level" of an analyte or "detecting" an analyte is used.

"Quantitative" assays in general provide information on the amount of an analyte in a sample relative to a reference (control), and are usually reported numerically, where a "zero" value can be assigned where the analyte is below the limit of detection. "Semi-quantitative" assays involve presentation of a numeric representation of the amount of the analyte in the specimen that is relative to a reference (e.g., a threshold, e.g., normal threshold or an abnormal threshold), where a "zero" value can be assigned where the analyte is below the limit of detection. In general, semi-quantitative results are compared against an accompanying reference interval to provide a qualitative interpretation of the result.

"Sensitivity" refers to the fraction of people with the disease or disease risk level (e.g., low risk prostate cancer) that a test correctly identifies as positive. "Specificity" refers to the fraction of people without the disease or disease risk level that the test correctly identifies as negative. The fractions with respect to sensitivity and/or specificity may be presented as a percentage. Where expressed as percentages, specificity can be calculated as by subtracting the sensitivity value for incorrect diagnosis from 100.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

The complement of a nucleic acid sequence as used herein refers to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

The terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease. Specific prostate cancer therapies of interest include, but are not limited to, active surveillance, surgery, irradiation, systemic chemotherapy, and the like. Suitable prostate cancer therapies are known in the art and described in, e.g., Suardi N, et al. (2008) *Cancer* 113:2068-2072; Heidenreich A, et al. (2008) *Eur Urol* 53:68-80; and in NCCN Clinical Practice Guidelines in Oncology Prostate Cancer, Version 1.2008; the disclosures of which are incorporated herein by reference.

Methods of Determining a Likelihood of Adverse Prostate Cancer Pathology

As summarized above, aspects of the present disclosure include methods for determining a likelihood of adverse prostate cancer pathology in a subject. Such a determination of the likelihood of adverse prostate cancer pathology may include computing a likelihood of adverse prostate cancer pathology in the subject so as to differentiate the subject from a healthy individual. A determination of the likelihood of adverse prostate cancer pathology can involve differentiating the subject from an individual with adverse prostate cancer pathology.

In general, the methods involve determining an amount of at least one diagnostic miRNA in a biological sample from the subject, comparing the amount of the at least one diagnostic miRNA with a reference amount, and generating a report indicating a likelihood of adverse prostate cancer pathology in the subject based on results of said comparing the amount of the at least one diagnostic miRNA with the reference amount. The detection of one or more such diagnostic miRNAs can be used to determine a likelihood of adverse prostate cancer pathology in a subject. The methods of the present disclosure also find use in facilitating treatment decisions for a subject.

The diagnostic miRNAs used in the methods of the present disclosure, as well as the methods of detection and analysis, are described in more detail below.

Diagnostic miRNAs for Detection

The methods of present disclosure involve detection of a diagnostic miRNA in a biological sample of a patient. Specifically, the present methods involve detection of mir-19a, mir-19b, mir-519c-5p, and/or mir-345.

In certain embodiments, the methods involve detection of one of mir-19a, mir-19b, and mir-519c-p. In other embodiments, the methods involve detection of mir-19a and mir-19b. In other embodiments, the methods involve detection of mir-19b and mir-519c-5p. In still other embodiments, the methods involve detection of mir-19a and mir-519c-5p. In certain embodiments, the methods involve detection of all three of mir-19a, mir-19b, and mir-519c-5p.

The methods can further involve detection of other biomarkers.

mir-19a

The diagnostic miRNA mir-19a, which may also be referred to as "hsa/mmu miR-19a" or "hsa-mir-19a," is a member of the mir-17-92 cluster (FIG. 3). Examples of the stem-loop sequence for hsa-mir-19a include those comprising a nucleic acid sequence of miRBase Accession No. MI0000073 and EntrezGene Gene ID 406979, and naturally occurring variants thereof. For example, the nucleic acid stem-loop sequence of MI0000073 is as follows:

(SEQ ID NO: 2839)
GCAGUCCUCUGUUAGUUUUGCAUAGUUGCACUACAAGAAGAAUGUAGUUG

UGCAAAUCUAUGCAAAACUGAUGGUGGCCUGC.

The stem-loop sequence may be processed to the mature sequence of mir-19a. Examples of the mature sequence include those comprising a nucleic acid sequence of miRBase Accession Nos. MIMAT0004490 and MIMAT0000073. For example, the nucleic acid sequence of MINIAT0004490 is as follows: AGUUUUGCAUAGUUG-CACUACA (SEQ ID NO:2840).

For example, the nucleic acid sequence of MIMAT0000073 is as follows:

UGUGCAAAUCUAUGCAAAACUGA.    (SEQ ID NO: 2841)

Figure 19A:
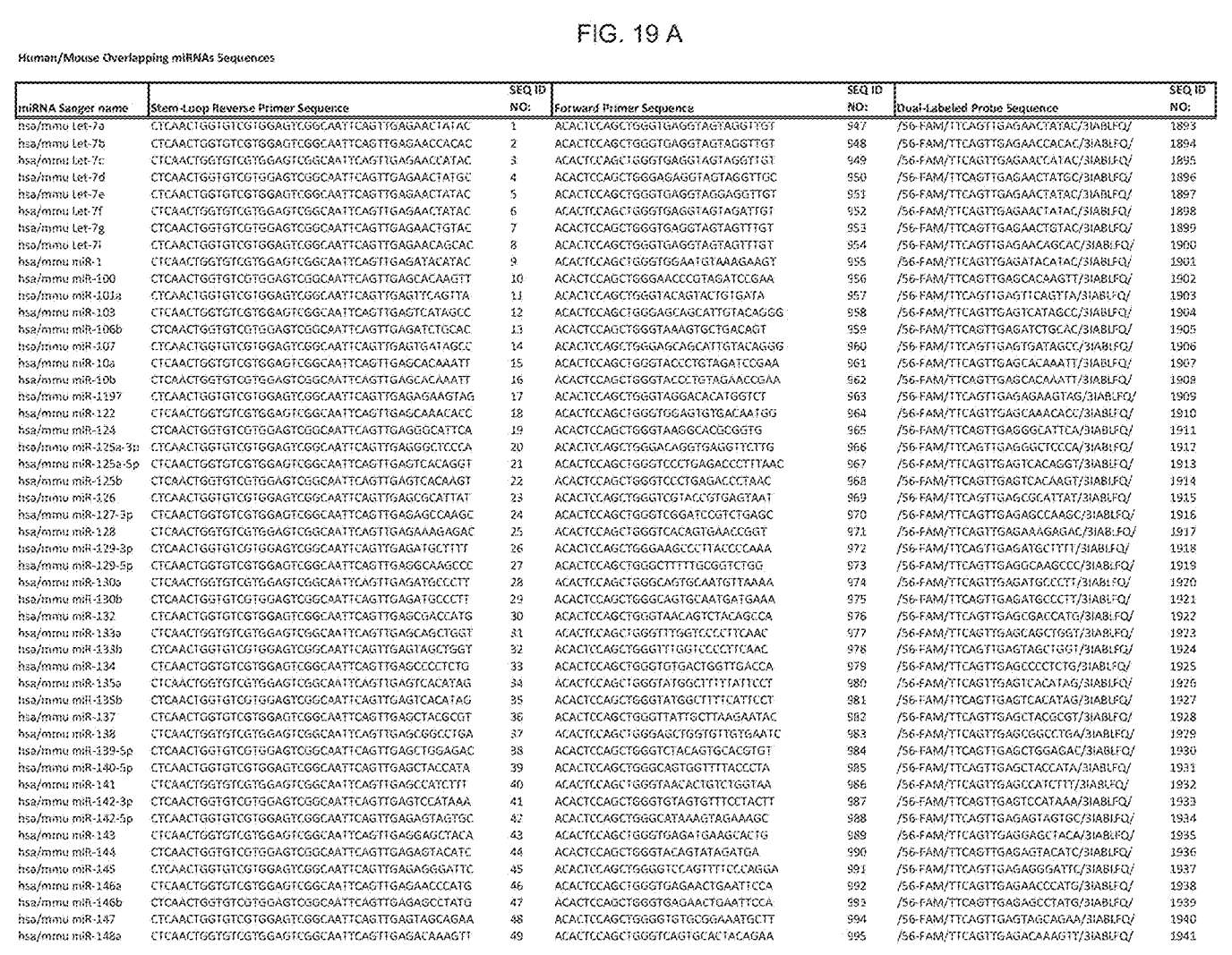
Figure 19A:
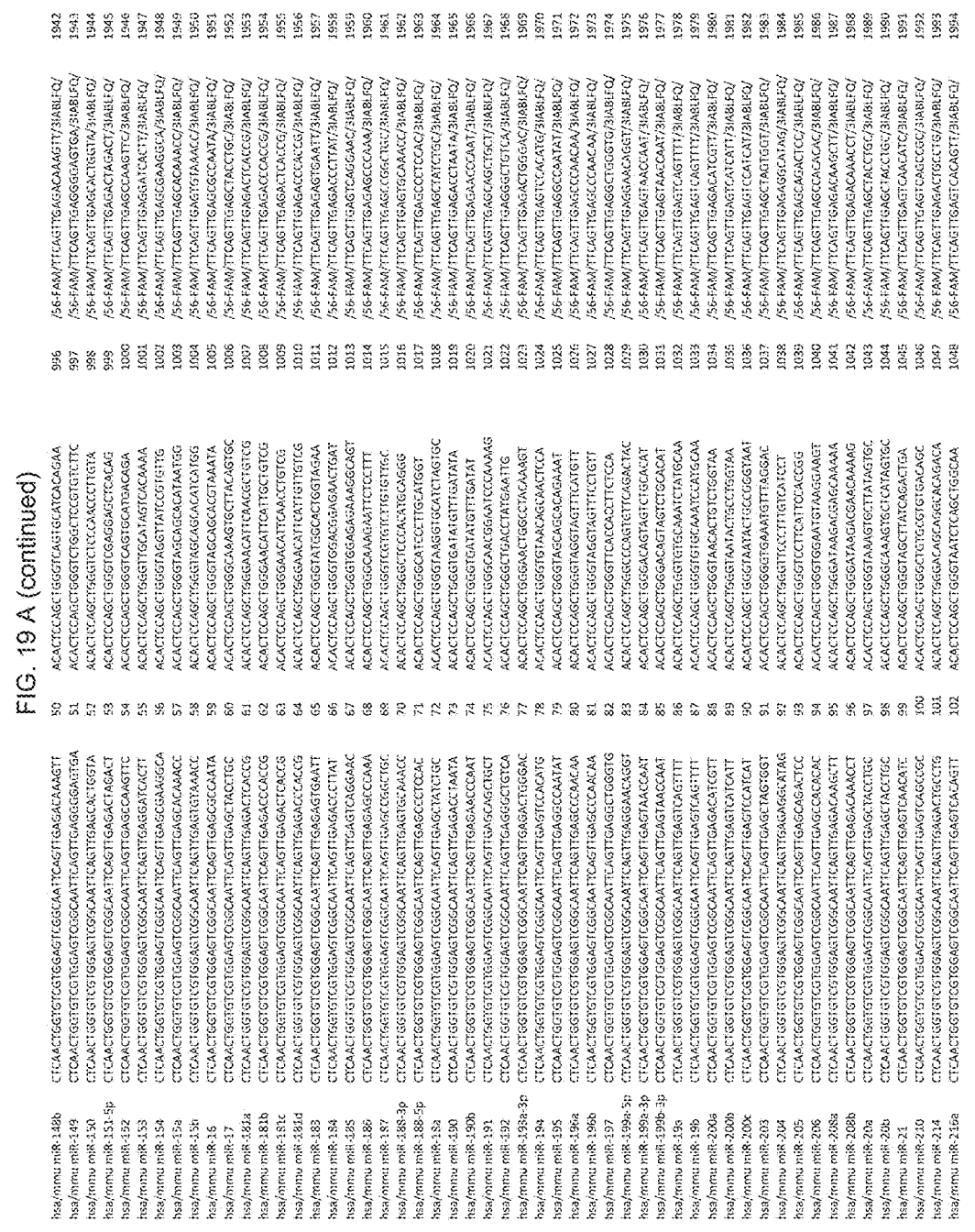
Figure 19A:
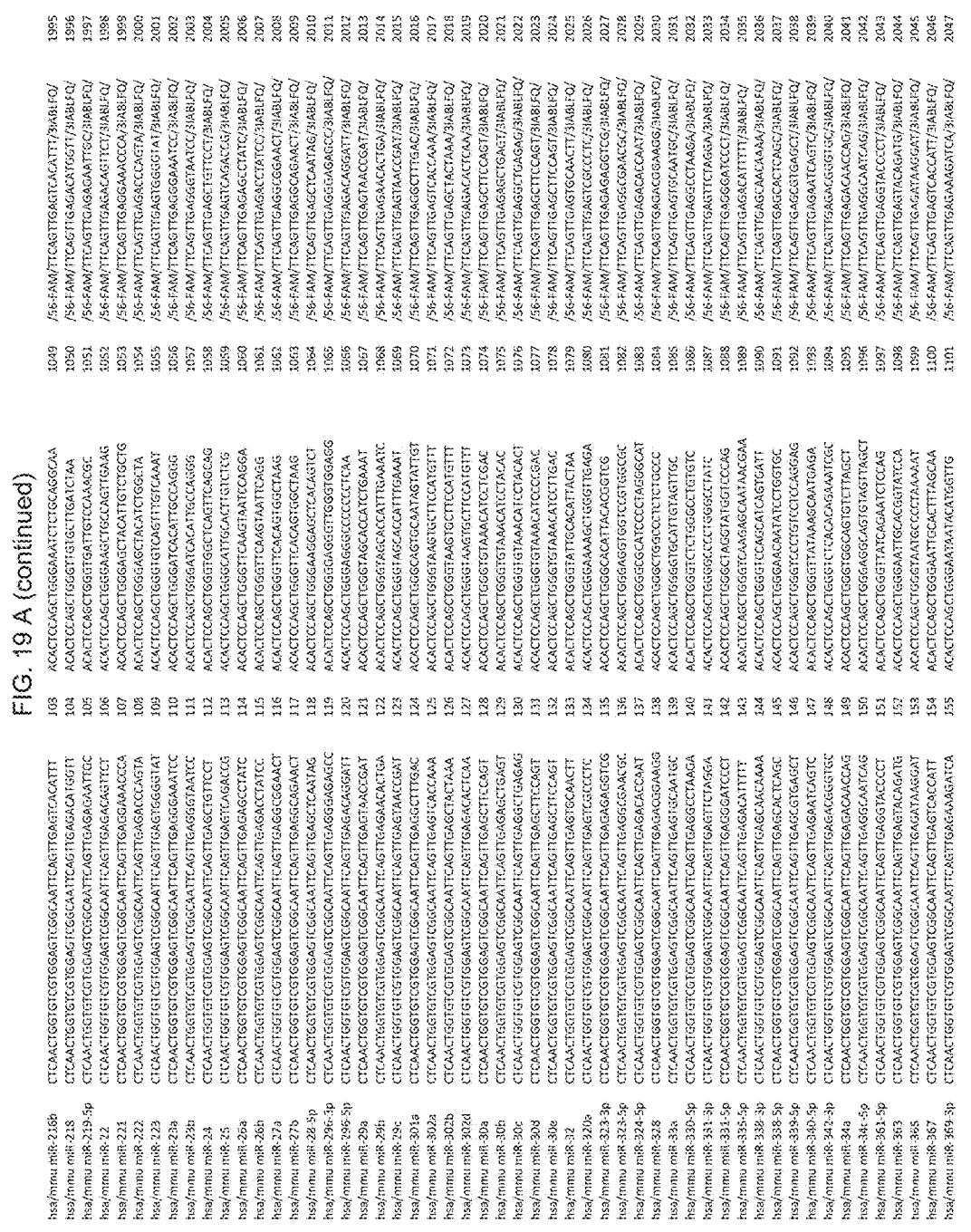
Figure 19:
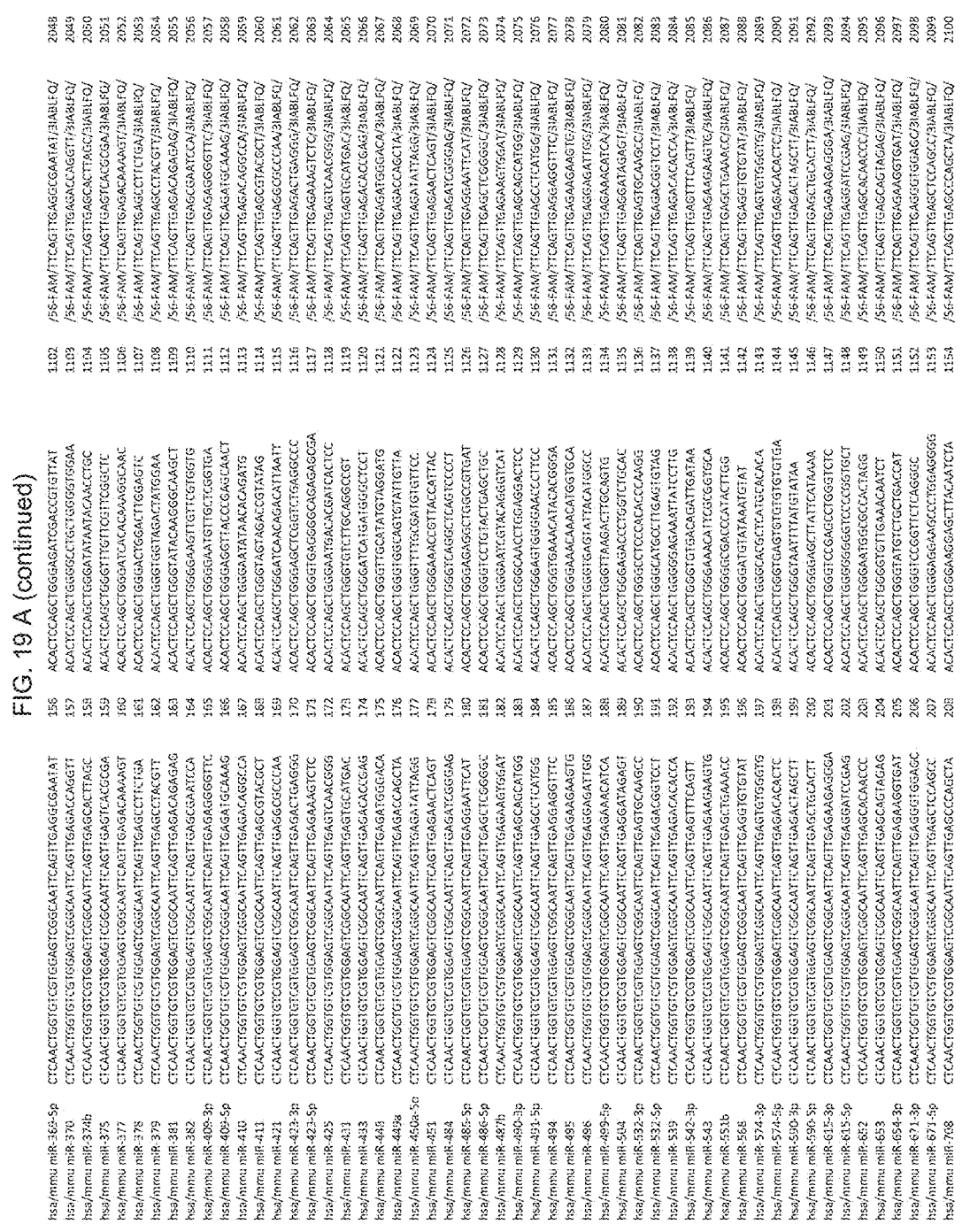
Figure 19B:
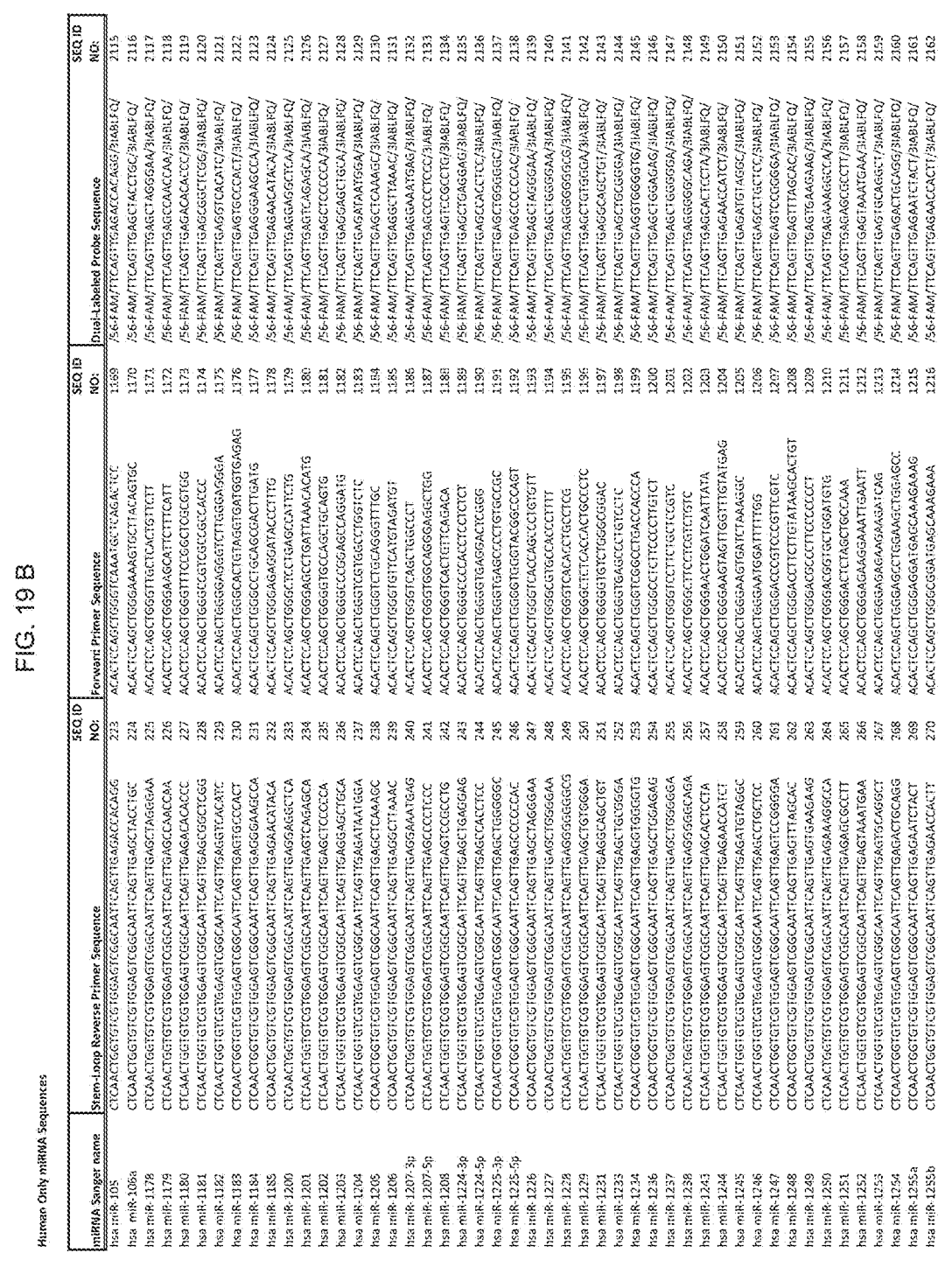
Figure 19:
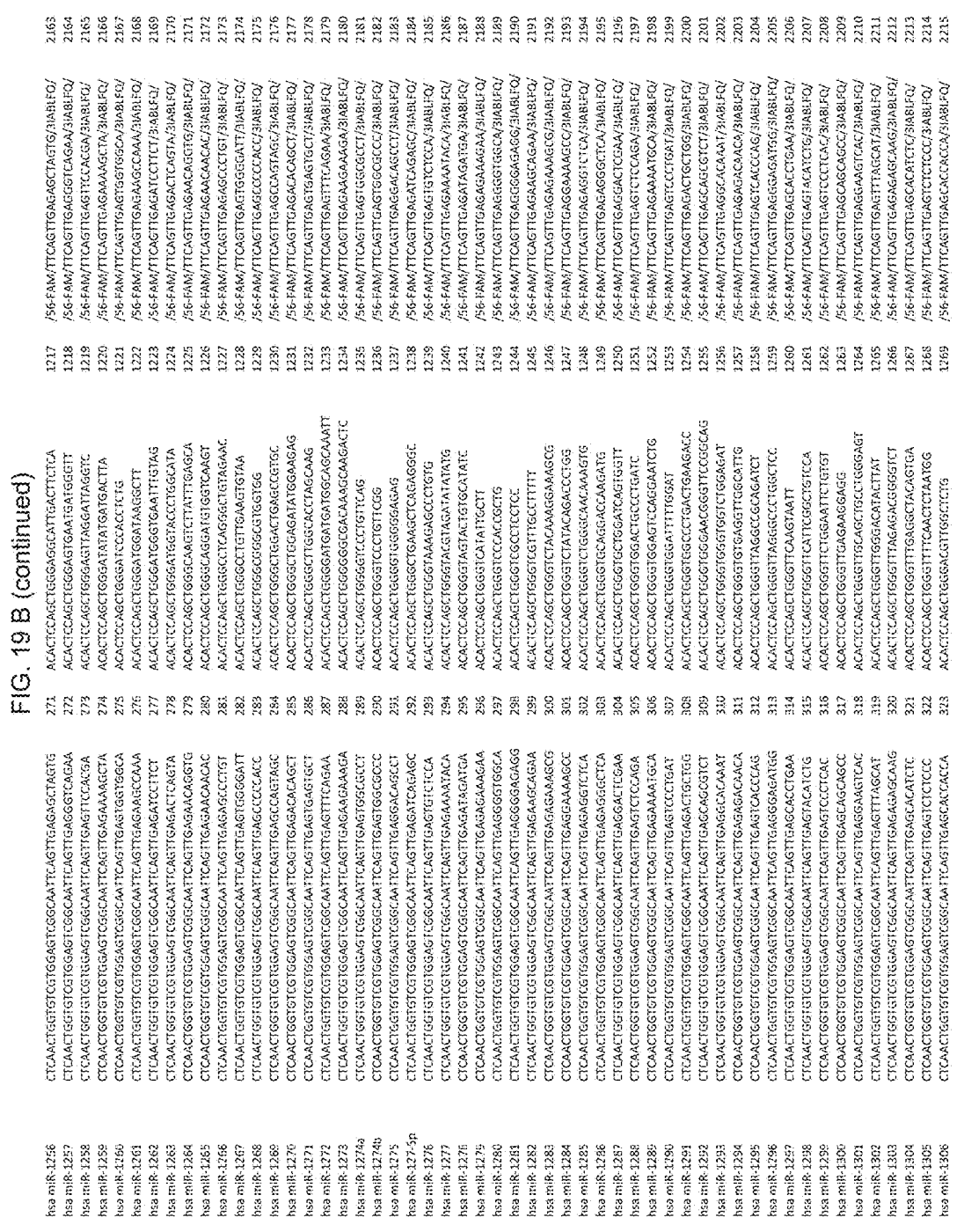
Figure 19:
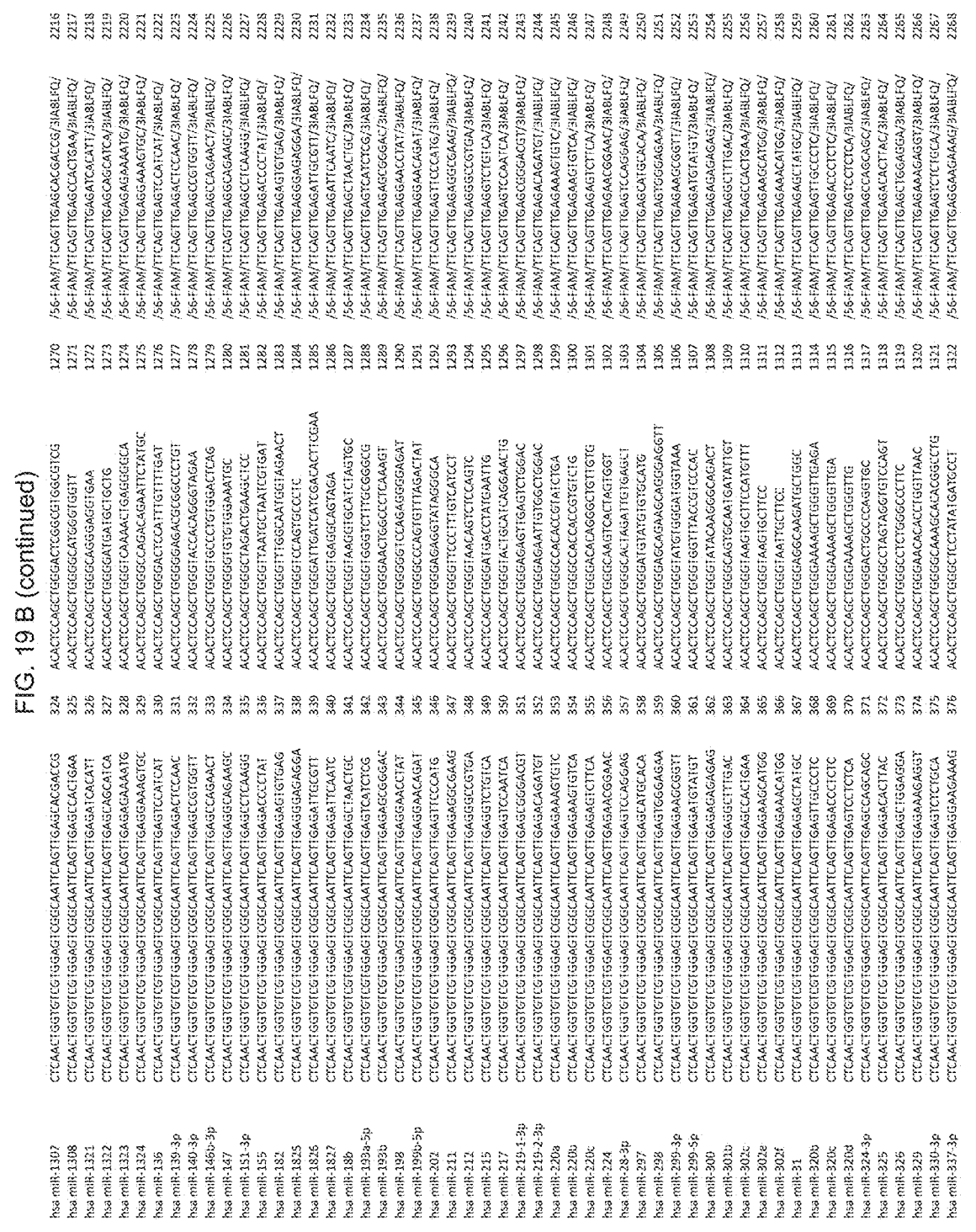
Figure 19:
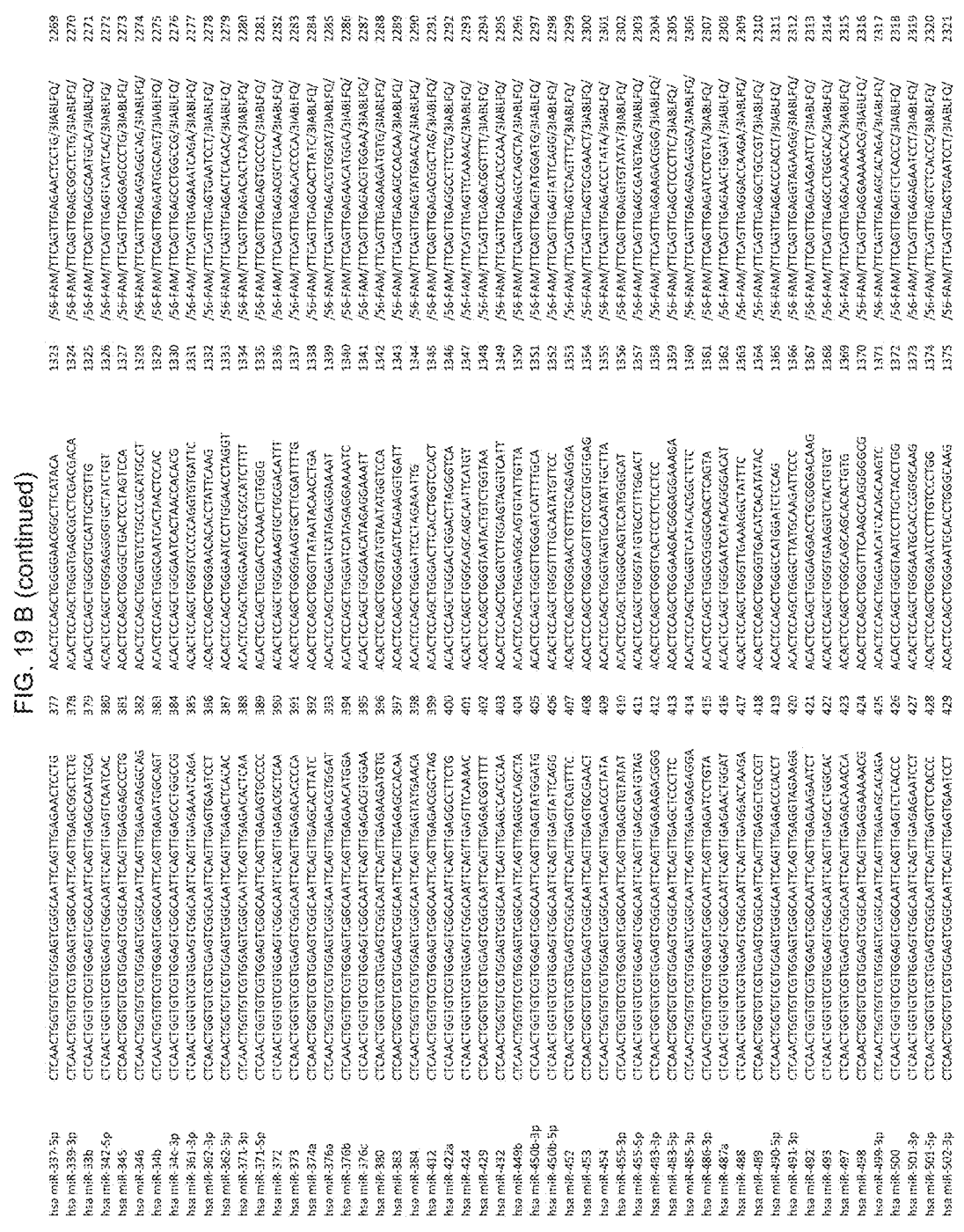
Figure 19:
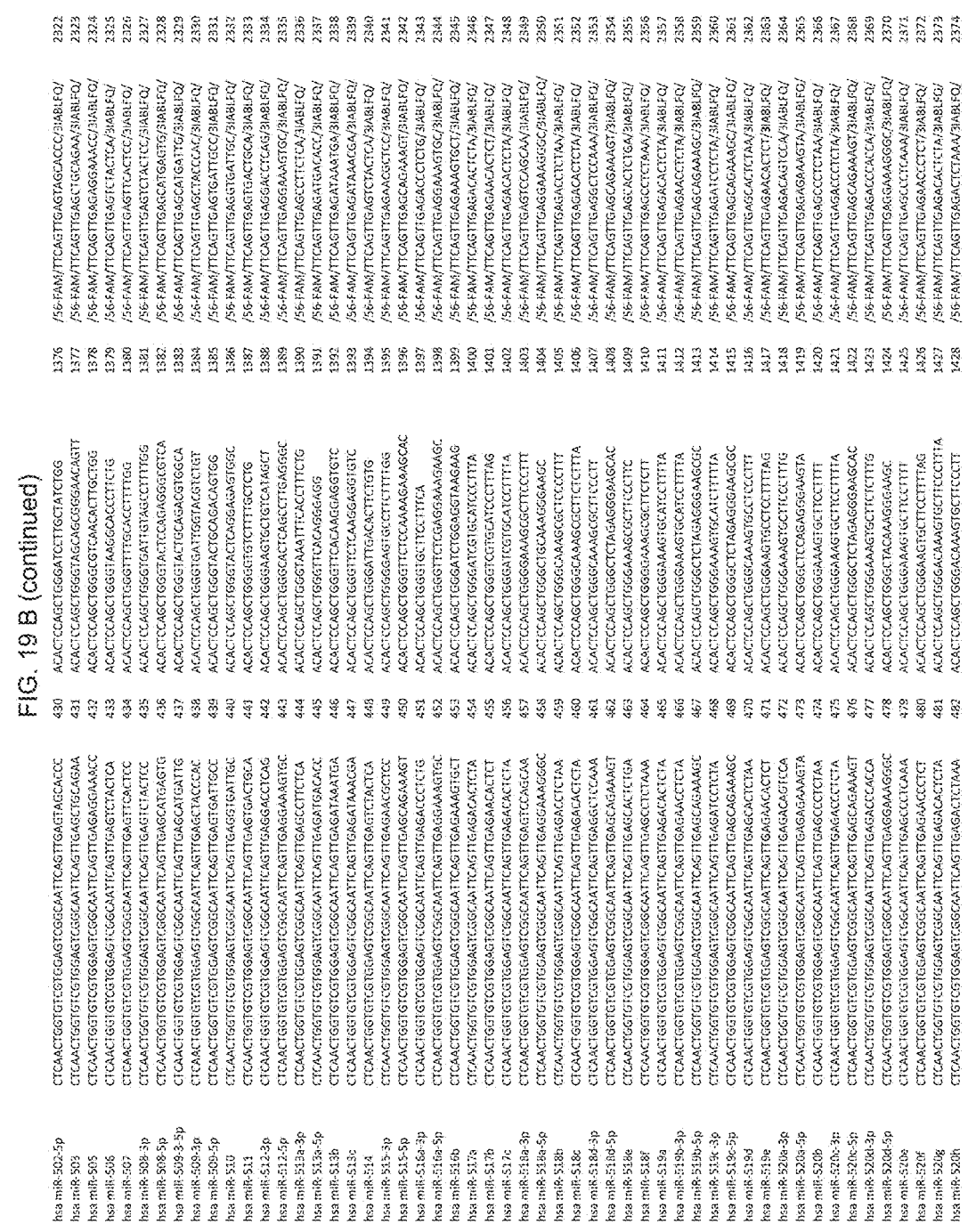
Figure 19:
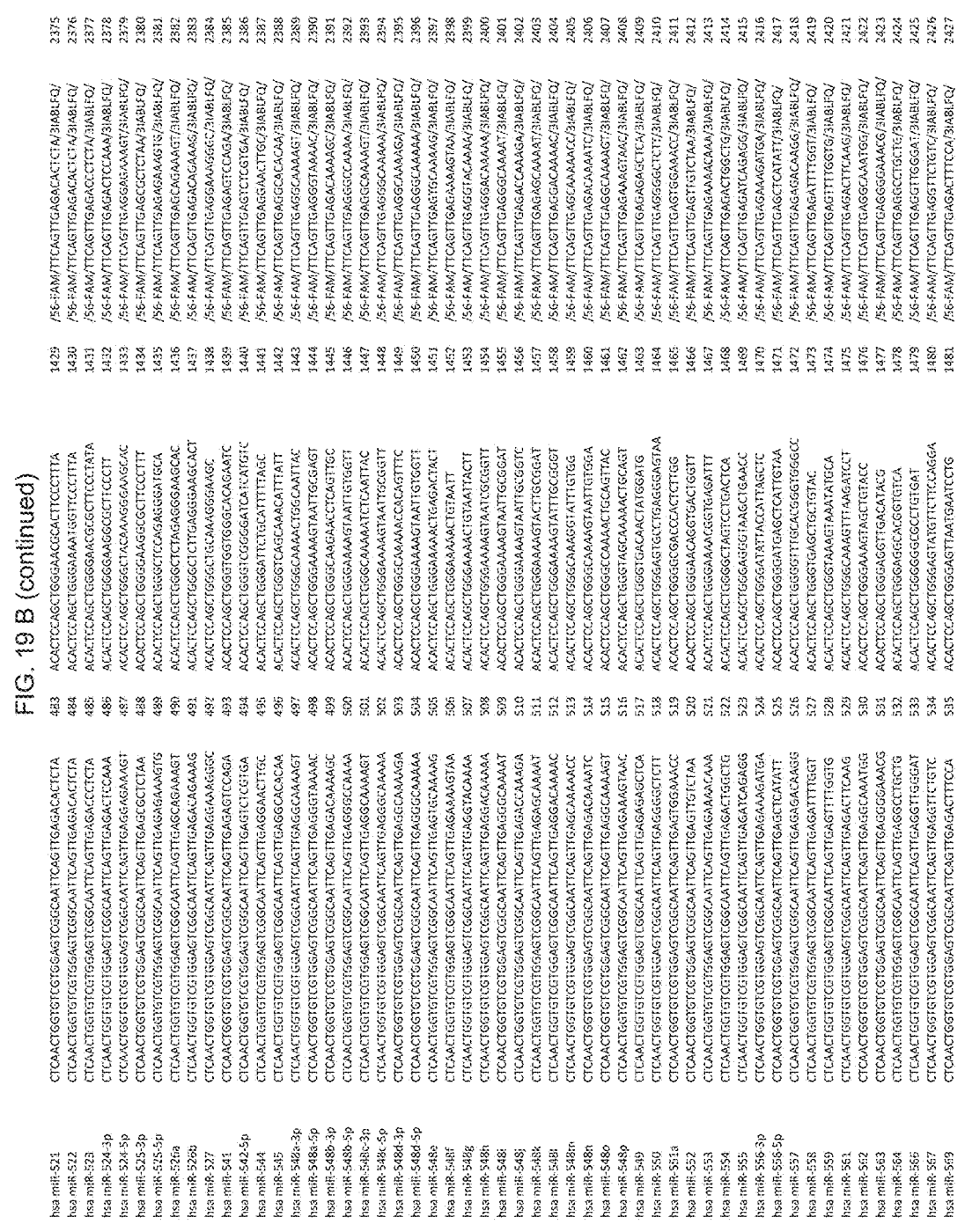
Figure 19:
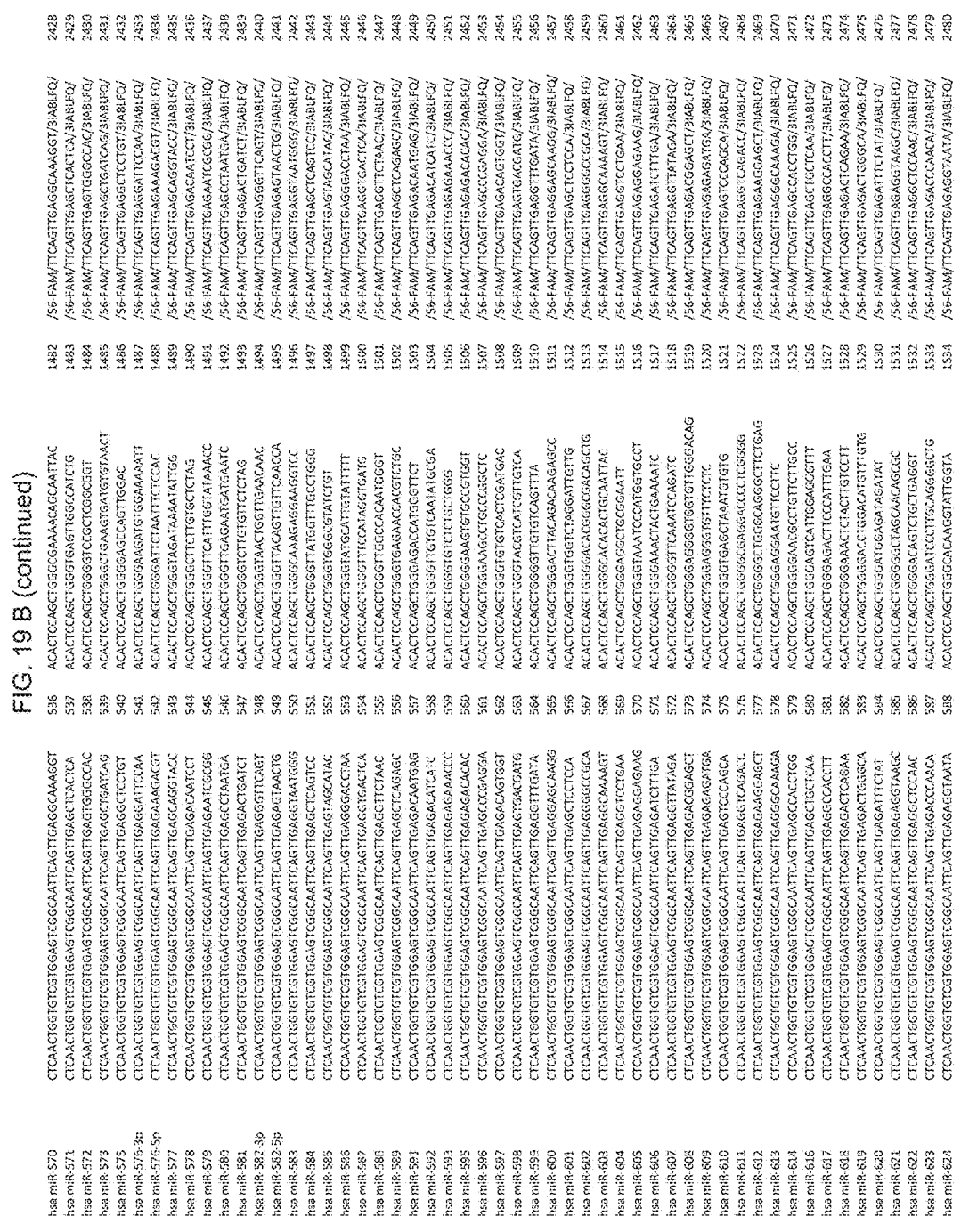
Figure 19:
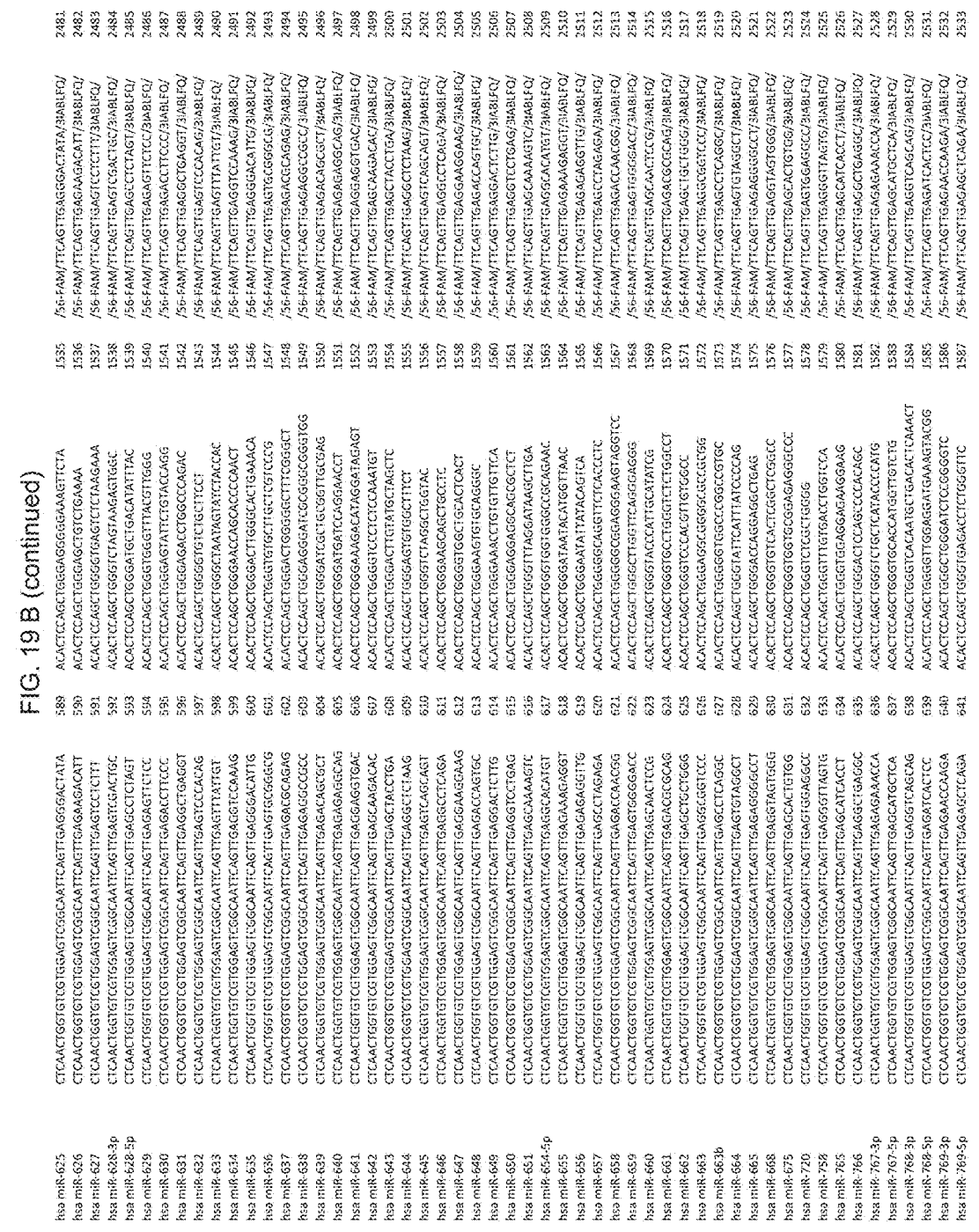
Figure 19C:
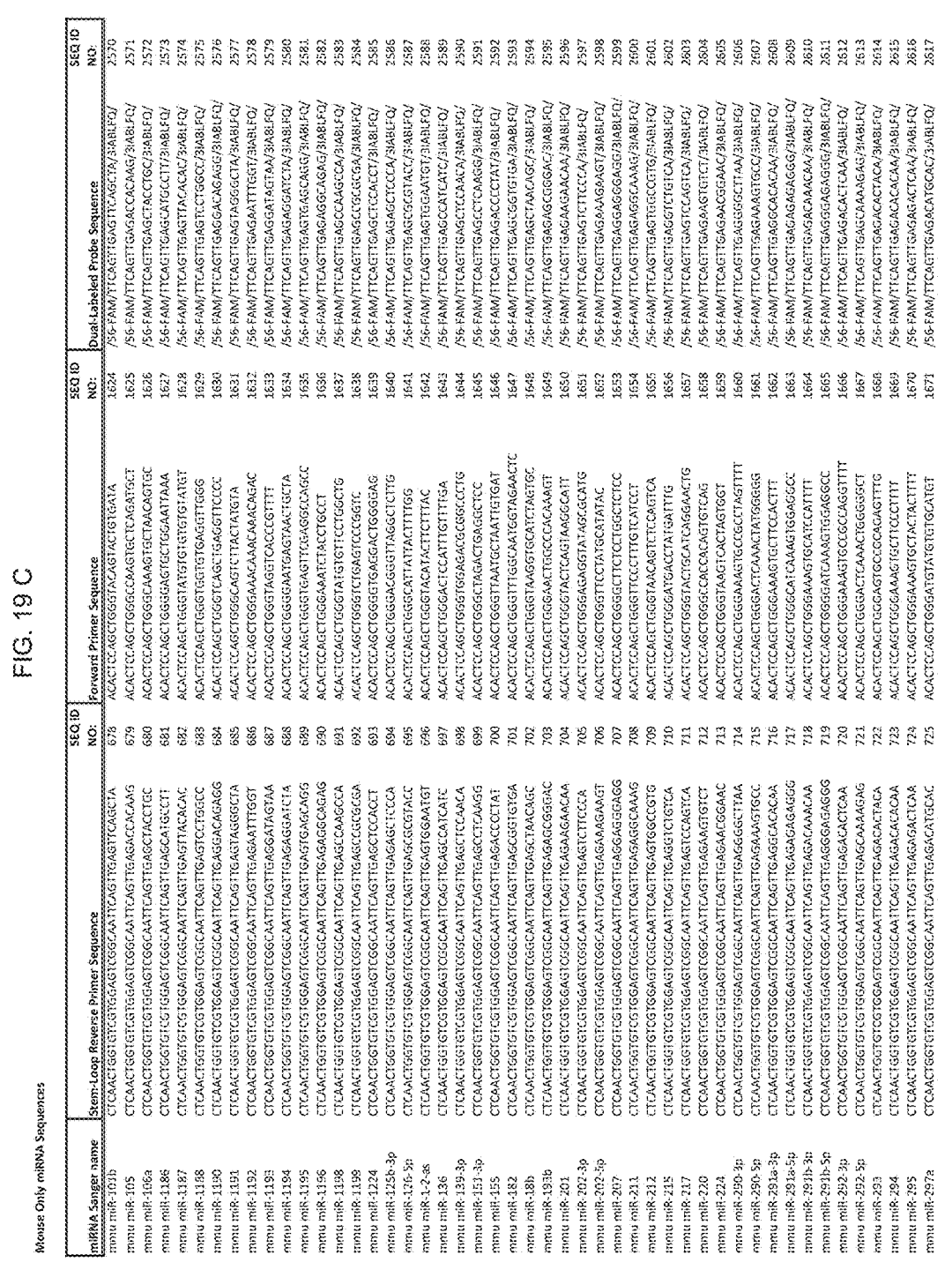
Figure 19:
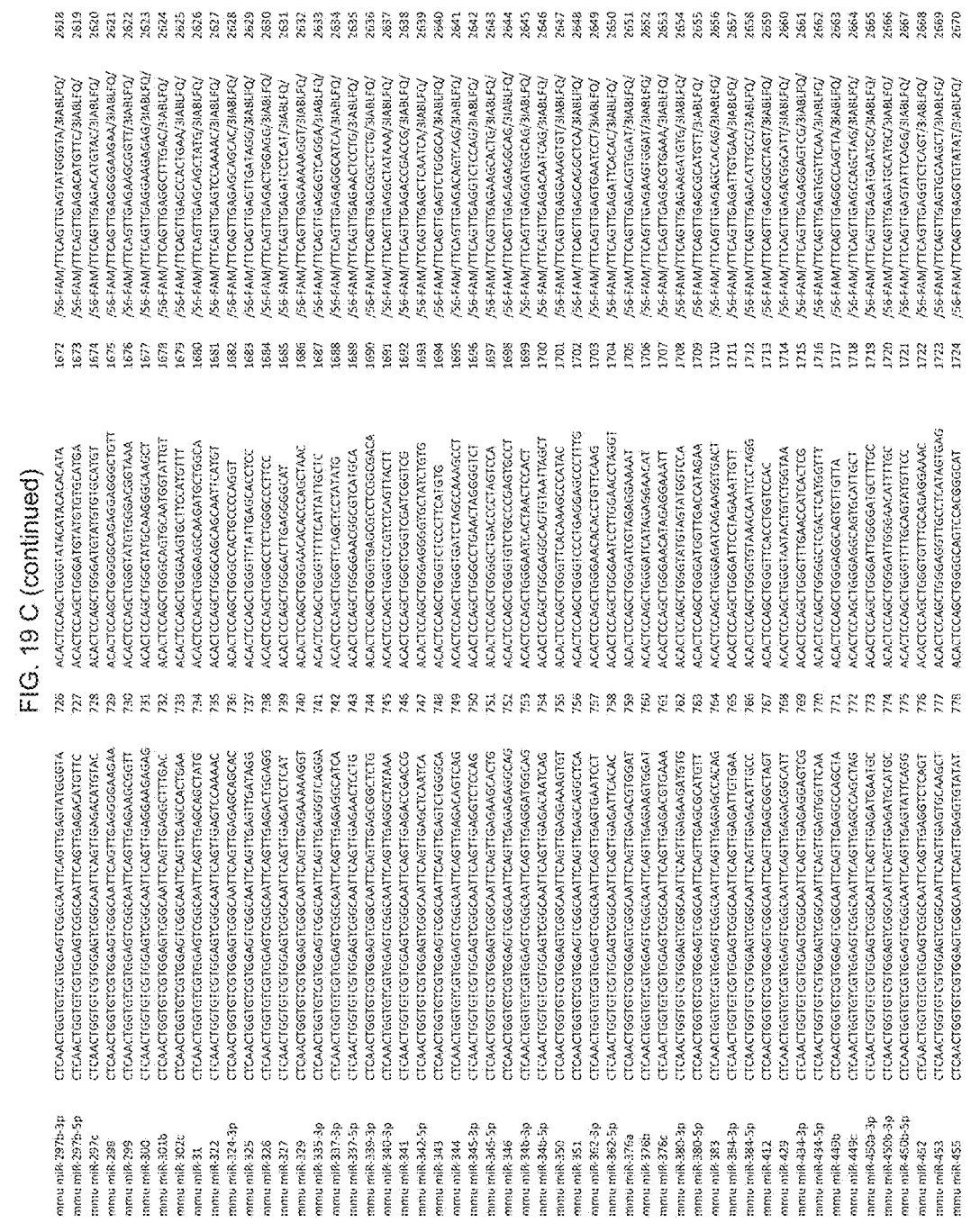
Figure 19C:
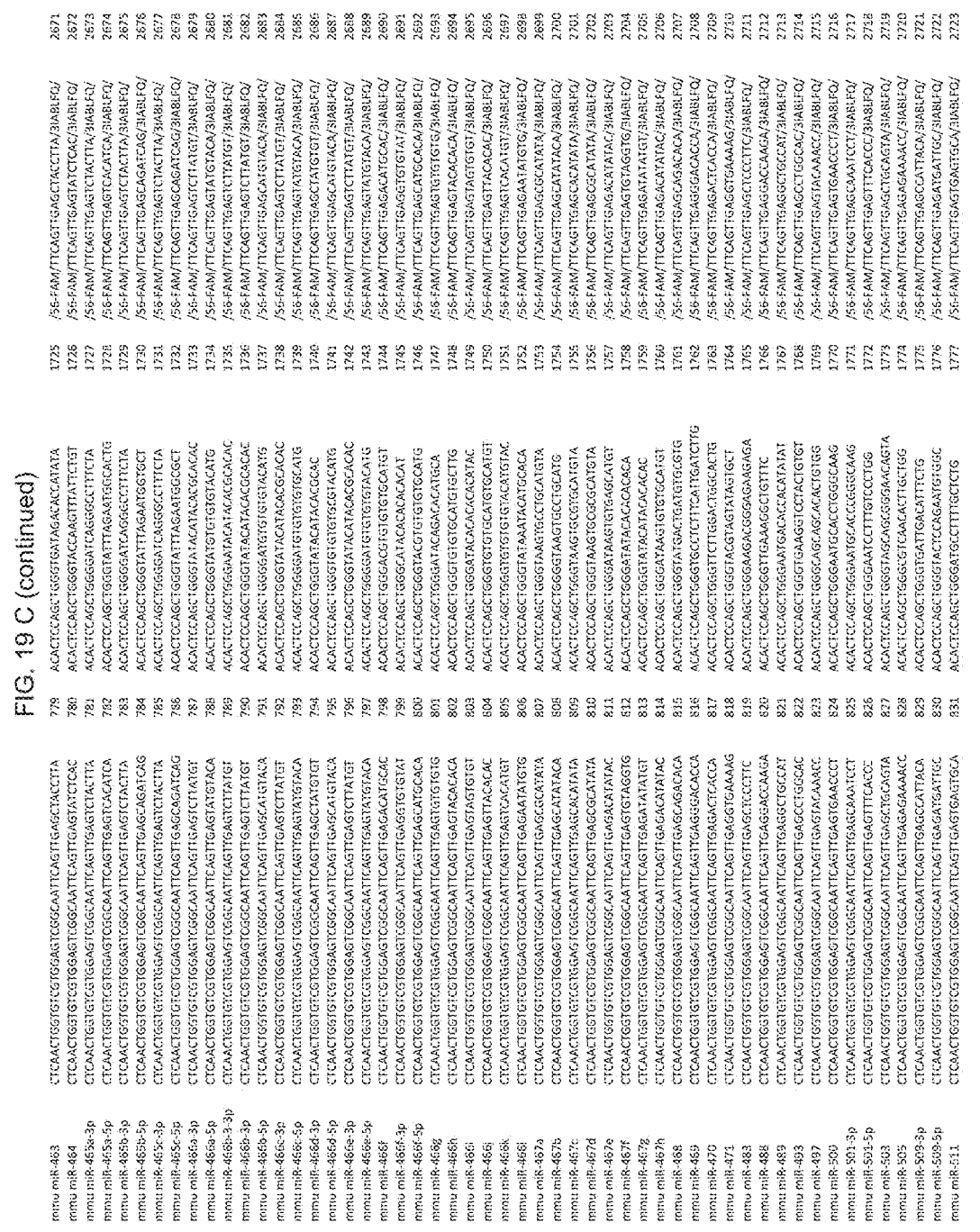
Figure 19:
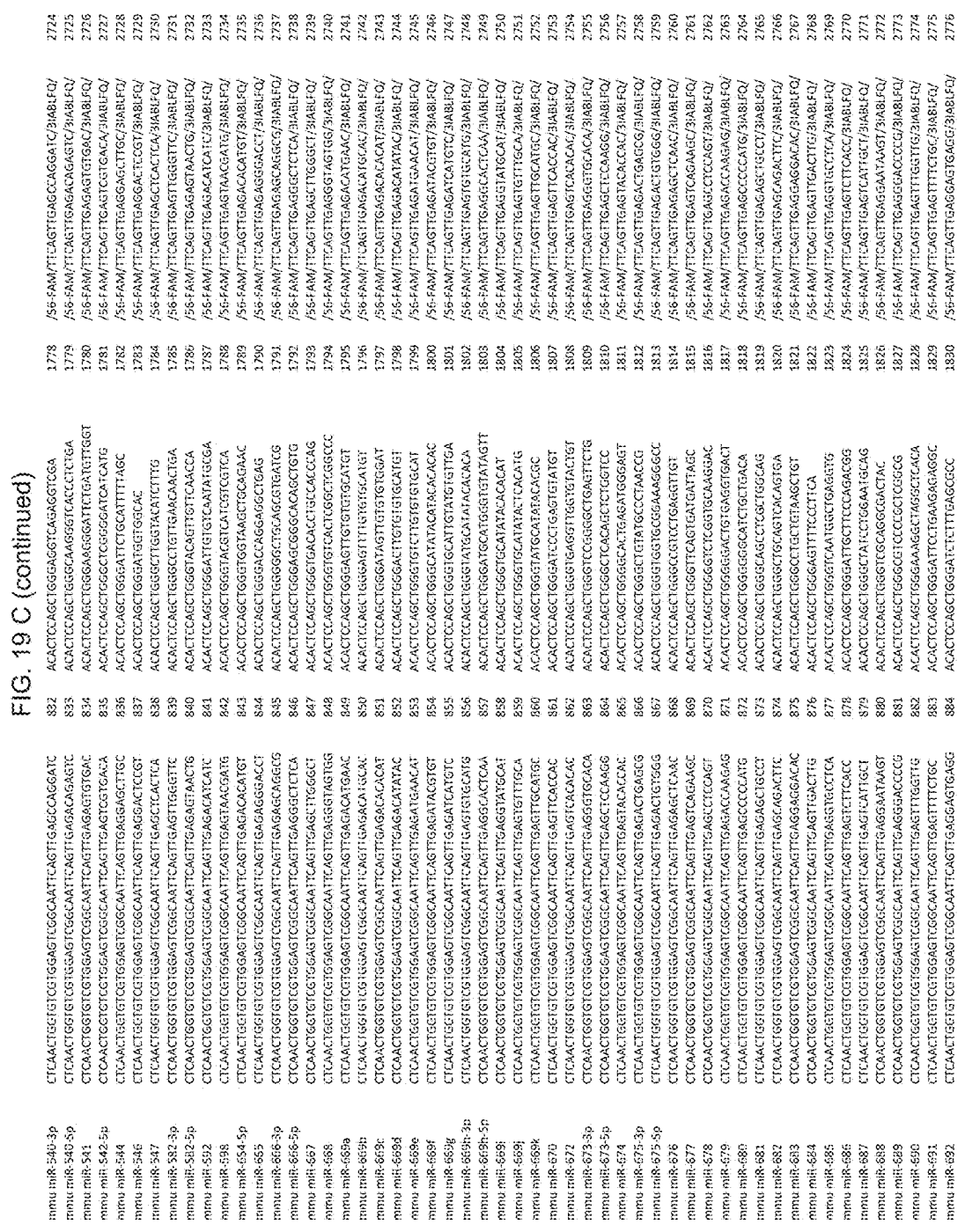
Figure 19:
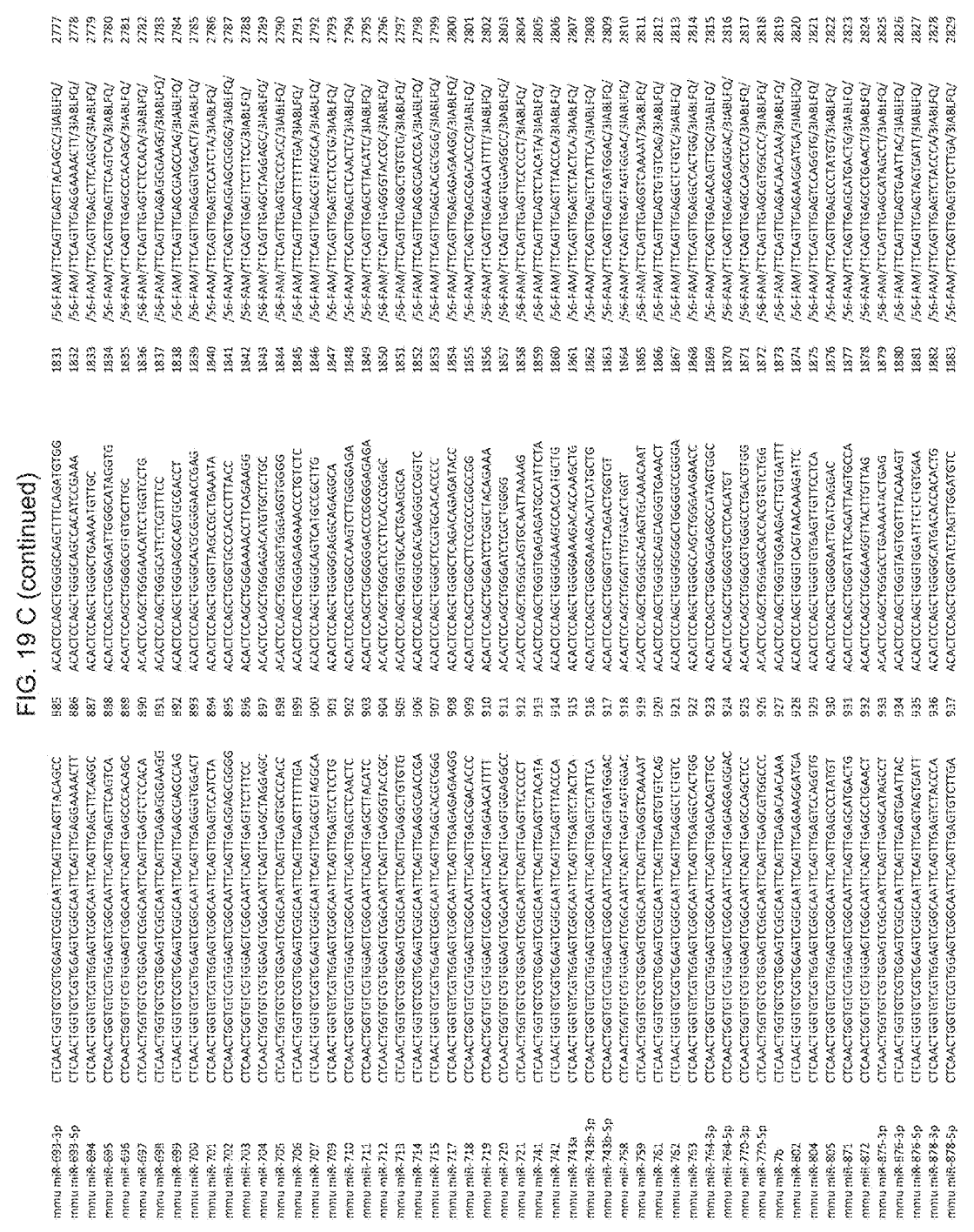

Detection of mir-19a encompasses detection of the mature miRNA, as well as detection of naturally occurring variants and fragments thereof found in a biological sample, and detection of a precursor molecule of the aforementioned miRNAs, such as the corresponding pri-miRNAs or pre-miRNAs. Detection of mir-19a can involve detection using one or more probes and/or primers, such as a probe or primer comprising SEQ ID NOs:86, 1032, or 1978 (FIG. 19).

mir-19b

The diagnostic miRNA mir-19b, which may also be referred to as "hsa/mmu miR-19b" or "hsa-mir-19b," is a member of the mir-17-92 cluster (FIG. 3). Examples of the stem-loop sequence for hsa-mir-19b include those comprising a nucleic acid sequence of miRBase Accession No. MI0000074 and EntrezGene Gene ID 406980, and naturally occurring variants thereof. For example, the nucleic acid stem-loop sequence of MI0000074 is as follows:

(SEQ ID NO: 2842)
CACUGUUCUAUGGUUAGUUUUGCAGGUUUGCAUCCAGCUGUGUGAUAUUC

UGCUGUGCAAAUCCAUGCAAAACUGACUGUGGUAGUG.

The stem-loop sequence may be processed to the mature sequence of mir-19b. Examples of the mature sequence include those comprising a nucleic acid sequence of miRBase Accession Nos. MIMAT0004491 and MIMAT0000074. For example, the nucleic acid sequence of MIMAT0004491 is as follows: AGUUUUGCAGGUUUG-CAUCCAGC (SEQ ID NO:2843).

For example, the nucleic acid sequence of MIMAT0000074 is as follows:

UGUGCAAAUCCAUGCAAAACUGA.    (SEQ ID NO: 2844)

Detection of mir-19b encompasses detection of the mature miRNA, as well as detection of naturally occurring variants and fragments thereof found in a biological sample, and detection of a precursor molecule of the aforementioned miRNAs, such as the corresponding pri-miRNAs or pre-miRNAs. Detection of mir-19b can involve detection using one or more probes and/or primers, such as a probe or primer comprising SEQ ID NOs:87, 1033, or 1979 (FIG. 19).

mir-519c-5p

The diagnostic miRNA mir-519c-5p, which may also be referred to as "hsa miR-519c-5p" or "hsa-mir-519c-5p," is a member of the mir-1283 cluster (FIG. 3). Examples of the stem-loop sequence for hsa-mir-519c-5p include those comprising a nucleic acid sequence of miRBase Accession No.

MI0003148 and EntrezGene Gene ID 574466, and naturally occurring variants thereof. For example, the nucleic acid stem-loop sequence of MI0003148 is as follows:

(SEQ ID NO: 2845)
UCUCAGCCUGUGACCCUCUAGAGGGAAGCGCUUUCUGUUGUCUGAAAGAA

AAGAAAGUGCAUCUUUUUAGAGGAUUACAGUUUGAGA.

The stem-loop sequence may be processed to the mature sequence of mir-519c-5p. Examples of the mature sequence include those comprising a nucleic acid sequence of miR-Base Accession No. MIMAT0002831. For example, the nucleic acid sequence of MIMAT0002831 is as follows: CUCUAGAGGGAAGCGCUUUCUG (SEQ ID NO:2846).

Detection of mir-519c-5p encompasses detection of the mature miRNA, as well as detection of naturally occurring variants and fragments thereof found in a biological sample, and detection of a precursor molecule of the aforementioned miRNAs, such as the corresponding pri-miRNAs or pre-miRNAs. Detection of mir-519c-5p can involve detection using one or more probes and/or primers, such as a probe or primer comprising SEQ ID NOs:469, 1415, or 2361 (FIG. 19).

mir-345

The diagnostic miRNA mir-345, which may also be referred to as "hsa-miR-345," is the predicted human homologue of a sequence cloned from rat neuronal tissue, later validated in human (FIG. 3). Examples of the stem-loop sequence for hsa-mir-345 include those comprising a nucleic acid sequence of miRBase Accession No. MI0000825 and EntrezGene Gene ID 442910, and naturally occurring variants thereof.

Reference miRNAs for Detection

In certain aspects, one or more reference miRNA(s) may be used to establish a reference amount against which an amount of a diagnostic miRNA may be compared.

Reference miRNAs may be detectable in a biological sample from a subject. Accordingly, specific reference miRNAs may vary depending on, e.g., the particular type of biological sample, the specific assay employed, purification and/or concentration steps, and other factors known to those of skill in the art.

Examples of reference miRNAs of interest include, but are not limited to, mir-17, mir-20a, mir-92a, mir-106a, mir-93, mir-25, let-7b, mir-24, mir-939, mir-1234, mir-522, mir-525-5p, mir-660, mir-941, mir-1274a, mir-1274b, mir-302f, mir-34c-3p, mir-663, mir-197, mir-223, mir-297, mir-346, mir-484, mir-486, mir-584, mir-638, mir-629, mir-720, mir-942, mir-1208, and mir-1243. The sequences of the mature miRNA forms of the foregoing reference miRNAs and their corresponding stem-loop sequences may be found, e.g., in the miRBase sequence database. The miRBase sequence database is described in Kozomara A, Griffiths-Jones S. (2011) *NAR* 39 (Database Issue):D152-D157; the disclosure of which is incorporated herein by reference.

In certain aspects, a plurality of reference miRNAs may be detected from a biological sample, such as 2 or more, including 10 or more, e.g., about 2 to 10, about 10 to 20, about 20 to 30, about 30 to 40, about 40 to 50, or about 50 to 100.

Detection of reference miRNAs encompasses detection of the mature miRNA, as well as detection of naturally occurring variants and fragments thereof found in a biological sample, and detection of a precursor molecule of the aforementioned miRNAs, such as the corresponding pri-miRNAs or pre-miRNAs. Detection of reference miRNAs can involve detection using one or more probes and/or primers, such as a probe or primer comprising: mir-17 (SEQ ID NOs: 60, 1006, or 1952), mir-20a (SEQ ID NOs: 97, 1043, or 1989), mir-92a (SEQ ID NOs: 664, 1610, 2556, 946, 1892, or 2838), mir-106a (SEQ ID NOs: 224, 1170, 2116, 680, 1626, or 2572), mir-93 (SEQ ID NOs: 218, 1164, or 2110), mir-25 (SEQ ID NOs: 113, 1059, or 2005), let-7b (SEQ ID NOs: 2, 948, or 1894), mir-24 (SEQ ID NOs: 112, 1058, or 2004), mir-939 (SEQ ID NOs: 671, 1617, or 2563), mir-1234 (SEQ ID NOs: 253, 1199, or 2145), mir-522 (SEQ ID NOs: 484, 1430, or 2376), mir-525-5p (SEQ ID NOs: 489, 1435, or 2381), mir-660 (SEQ ID NOs: 623, 1569, or 2515), mir-941 (SEQ ID NOs: 673, 1619, or 2565), mir-1274a (SEQ ID NOs: 289, 1235, or 2181), mir-1274b (SEQ ID NOs: 290, 1236, or 2182), mir-302f (SEQ ID NOs: 366, 1312, or 2258), mir-34c-3p (SEQ ID NOs: 384, 1330, or 2276), mir-663 (SEQ ID NOs: 626, 1572, or 2518), mir-197 (SEQ ID NOs: 82, 1028, or 1974), mir-223 (SEQ ID NOs: 109, 1055, or 2001), mir-297 (SEQ ID NOs: 358, 1304, or 2250), mir-346 (SEQ ID NOs: 382, 1328, 2274, 752, 1698, or 2644), mir-484 (SEQ ID NOs: 179, 1125, or 2071), mir-584 (SEQ ID NOs: 551, 1497, or 2443), mir-638 (SEQ ID NOs: 603, 1549, or 2495), mir-629 (SEQ ID NOs: 594, 1540, or 2486), mir-720 (SEQ ID NOs: 632, 1578, 2524, 911, 1857, or 2803), mir-942 (SEQ ID NOs: 674, 1620, or 2566), mir-1208 (SEQ ID NOs: 242, 1188, or 2134), and mir-1243 (SEQ ID NOs: 257, 1203, or 2149) (FIG. 19).

Subjects

The methods of the present disclosure can be used to determine a likelihood of adverse prostate cancer pathology in a male subject. The subject can be any subject having, suspected of having, or at risk of, prostate cancer, and includes subjects having, suspected of having, or at risk of having any proliferative lesion or abnormality of the prostate. Subjects include patients undergoing therapy, e.g., undergoing therapy to treat suspected or diagnosed prostate cancer or undergoing therapy which places the subject at risk of developing prostate cancer.

Subjects to be tested using a method of the present disclosure include individuals who present with or have presented with one or more symptoms of prostate cancer. Examples of such symptoms include any symptoms indicative of prostate cancer such as trouble urinating, decreased force in the stream of urine, blood in the urine, blood in the semen, swelling in the legs, discomfort in the pelvic area, bone pain, and/or any abnormal levels of PSA.

Subjects at risk prostate cancer include aged subjects (e.g., 50 or older, or 65 or older), subjects of particular races (e.g., black), and subjects with a family history of cancer, including prostate cancer.

Biological Samples

Suitable biological samples useful in the methods of the present disclosure include biological fluids (e.g., a blood sample, e.g., whole blood, blood fraction (e.g., serum, plasma)), and other liquid samples of biological origin, as well as solid tissue samples such as a liver biopsy specimen. Where the biological sample is a blood sample, the blood sample can be obtained from fresh blood or stored blood (e.g. in a blood bank). The biological sample can be a blood sample expressly obtained for an assay of the present disclosure or a blood sample obtained for another purpose which can be subsampled for an assay of the present disclosure.

Samples can be manipulated after procurement, such as by treatment with reagents, solubilization, and/or enrichment for certain components for an analyte(s) to be assayed. Samples can be pretreated as necessary by dilution in an appropriate buffer solution, concentrated if desired, or fractionated by any number of methods including but not limited to ultracentrifugation, fractionation by fast performance liquid chromatography (FPLC), or precipitation. For example, in certain aspects the sample is subfractionated into, e.g., vesicular and non-vesicular components (e.g. naked ribonucleoproteins) before subsequent analysis. Suitable means of sub-fractioning a sample are known in the art and described in, e.g., Duttagupta R, et al. (2011) *PLoS ONE* 6(6): e20769; the disclosure of which is incorporated herein by reference. Any of a number of standard aqueous buffer solutions, employing one of a variety of buffers, such as phosphate, Tris, or the like, at physiological pH can be used. In general, after isolation, samples (such as blood samples) are stored at −80° C. until assaying.

Assay Formats and Detection Methods

Biomarkers for analysis in connection with the methods of the present disclosure (e.g., mir-19a, mir-19b, and/or mir-519c-5p) can be detected using a variety of methods, with methods suitable for quantitative and semi-quantitative assays being of particular interest. Examples of detection methods include, but are not limited to, various assays involving reverse transcription of RNA and nucleic acid amplification (e.g., PCR, quantitative real time PCR, nucleic acid microarrays, sequencing, bead arrays, and the like).

For example, isolated miRNA from a biological sample can be used in hybridization or amplification assays that include, but are not limited to, Southern or Northern analyses, polymerase chain reaction (PCR) analyses and probe arrays. One method for the detection of miRNA levels involves contacting the isolated miRNA with a nucleic acid molecule (probe) that can hybridize to biomarker-encoding nucleic acid. The nucleic acid probe can be for example, a full-length cDNA, or a portion thereof, such as an oligonucleotide of at least 7, 15, 30, 50, 100, 250 or 500 nucleotides in length and sufficient to specifically hybridize under stringent conditions to biomarker-encoding nucleic acid. Examples of suitable probes include, but are not limited to, probes listed in FIG. 19 (e.g., SEQ ID NOs: 1-2838).

In one embodiment, the miRNA from a biological sample is immobilized on a solid surface and contacted with a probe. In an alternative embodiment, the probe(s) are immobilized on a solid surface and the miRNA isolated from the biological sample is contacted with the probe(s), e.g., as in an array format.

Methods of detecting levels of biomarker expression in a sample can involve any suitable method of nucleic acid amplification, e.g., by RT-PCR, ligase chain reaction, or any other nucleic acid amplification method, followed by the detection of the amplified molecules using techniques well known to those of skill in the art. In one example, biomarker expression is assessed by quantitative fluorogenic RT-PCR (e.g., such as using TaqMan™, SYBR Green, and the like). Such methods typically utilize pairs of oligonucleotide primers that are specific for a biomarker-encoding nucleic acid. Methods for designing oligonucleotide primers specific for a known sequence are well known in the art.

In certain embodiments, the method employs a detection approach that involves multiplex qRT-PCR, such as the microfluidic-based multiplex qRT-PCR method as described in Moltzahn, et al. (2010) *Cancer Res* 71:550-560; the disclosure of which is incorporated herein by reference. Detection methods of interest further include, but are not limited to, those described in Mitchell P S, et al. (2008) *PNAS* 105(30):10.513-10518 and U.S. Patent Publication Nos. 2011/0275534 and 2012/0264638 the disclosures of which are incorporated herein by reference.

Determination of a Likelihood of Adverse Prostate Cancer Pathology

The methods of the present disclosure include methods for determining a likelihood of adverse prostate cancer pathology in a subject. Such methods generally involve determining an amount of at least one diagnostic miRNA using an assay or detection method as described herein). The amount of the diagnostic miRNA(s) may be compared with a reference amount, and the results of the comparison may be used to indicate the likelihood of adverse prostate cancer pathology in the subject.

In certain aspects, a reference amount is calculated using the level of one or more miRNA(s). In certain aspects, a reference amount is instead, or also, calculated using one or more biomolecule(s) that are not miRNA(s), such as polypeptides (e.g., peptides, proteins, etc.), and/or nucleic acids (e.g., DNA, long non-coding RNA molecules, small RNA(s), spiked-in RNAs, etc.).

In certain aspects, the reference amount may be a control amount of the diagnostic miRNA, such as the amount of the diagnostic miRNA in a healthy individual or a population of healthy individuals. The reference amount may, in some aspects, be the amount of the diagnostic miRNA from a different individual or group of individuals, such as a control population that does not have adverse prostate cancer pathology, e.g., a control population as described in Examples.

In some embodiments, the reference amount is an amount of the diagnostic miRNA from the same subject, measured at a prior time point. For instance, the prior time point may be a time point that is prior to the subject exhibiting clinical presentations of prostate cancer and/or at an earlier stage of the disease.

Embodiments further include calculating the reference amount from the amounts of a plurality of reference miRNAs. For example, the reference amount may be calculated from cycle threshold (Ct) values of a plurality of reference miRNAs from the biological sample, such as by computing a normalized Ct value, such as by computing a mean, and/or median Ct value from the plurality. Any convenient means of normalizing, e.g., a Ct value may be employed in calculating the reference amount. In certain aspects, a comparison may include the use of a model, such as a logistic regression model, classification tree model, random forest classification model, and the like.

Embodiments further include calculating the reference amount using spike-in small RNAs. The use of such spike-in small RNAs are described in, e.g., Cronin M, et al. (2004) *Clin. Chem* 50(8):1464-1471 and M N McCall and R A Irizarry (2008) *Nucleic Acids Res.* 36(17): e108; the disclosures of which are incorporated by reference.

In some embodiments, a reference amount is determined using one or more of the method(s) described in Peltier H J and Latham G J (2008) *RNA* 4(5):844-852; Timoneda O, et al. (2012) *PLoS One* 7(9):e44413; Meyer S U, et al. (2012) *PLoS One* 7(6):e38946; Wylie D, et al. (2011) *BMC Res Notes* 4:555; Kirschner M B, et al. (2011) *PLoS One* 6(9):e24145; Roa W, et al. (2010) *Clin Invest Med* 33(2): E124; Schaefer A, et al. (2010) *Exp. Mol. Med.* 42(11):749-58; Galiveti C R, et al. (2010) *RNA* 16(2):450-461; Bissels U, et al. (2009) *RNA* 15(12):2375-2384; Mestdagh P, et al. (2009) *Genome Biol.* 10(6):R64; and/or variant(s) or comparable method(s) to the method(s) of any of the foregoing, the disclosures of which are incorporated herein by reference.

In addition to the amount of one or more diagnostic miRNA(s), methods of the present disclosure may involve the use of one or more additional risk factors to determine a likelihood of adverse prostate cancer pathology. Such additional risk factors include factors that may be ascertained without a biopsy of the subject (e.g., a biopsy of the subject's prostate). Such risk factors include, but are not limited to, the subject's age, race, PSA level, clinical stage, and the like. Accordingly, in such embodiments the subject methods may be performed on a subject without requiring a biopsy of the subject.

Additional risk factors of interest further include risk factors that require a biopsy. Such risk factors include, but are not limited to, the subject's primary biopsy Gleason score, secondary biopsy Gleason score, Gleason score sum, percentage cancer in biopsy cores, and the like.

The amounts of diagnostic miRNA(s) and/or one or more additional risk factors may be combined to provide an assessment of the likelihood of adverse prostate cancer pathology in a subject. For example, the diagnostic miRNA(s) can be combined with one or more risk factors as described above in an algorithm, which facilitates an assessment of the likelihood of adverse prostate cancer pathology in a subject.

For example, the likelihood of adverse prostate cancer pathology can be based on an algorithm generally described as follows:

$$\text{Score} = (+1 \text{ if } mir\text{-}19a > X_{mir\text{-}19a} \text{ or } mir\text{-}19b > X_{mir\text{-}19b}) + \quad \text{(Algorithm I)}$$
$$(+1 \text{ if } mir\text{-}519c\text{-}5p < X_{mir\text{-}519c\text{-}5p}) +$$
$$(+1 \text{ if } mir\text{-}345 < X_{mir\text{-}345})$$

where
$X_{mir\text{-}19a}$ is a reference amount for mir-19a.
$X_{mir\text{-}19b}$ is a reference amount for mir-19b,
$X_{mir\text{-}519\text{-}5p}$ is a reference amount for mir-519c-5p, and
$X_{mir\text{-}345}$ is a reference amount for mir-345.

In certain embodiments, $X_{mir\text{-}19a} = X_{mir\text{-}19b} = X_{mir\text{-}519c\text{-}5p} = X_{mir\text{-}345}$. For example, in embodiments where a reference amount is calculated from the amounts of a plurality of reference miRNAs, $X_{mir\text{-}19a}$, $X_{mir\text{-}19b}$, $X_{mir\text{-}519c\text{-}5p}$, and $X_{mir345}$ may be equivalent. In Algorithm I and the algorithms presented below, the higher the Score, the greater the likelihood of adverse prostate cancer pathology in the subject.

In certain aspects, the likelihood of adverse prostate cancer pathology is based on an algorithm that may be generally described as follows:

Score=(Algorithm I)+(1 if subject's age≥50)    (Algorithm II)

In certain aspects, the likelihood of adverse prostate cancer pathology is based on an algorithm that may be generally described as follows:

Score=(Algorithm I or II)+(1 if subject's clinical stage is T3a)    (Algorithm III)

In certain aspects, the likelihood is based on an algorithm that may be generally described as follows:

Score=(Algorithm I, II, or III)+(1 if subject's PSA level is between 6.1 and 10.0)+(2 if subject's PSA level is between 10.1 and 20.0)+(3 if subject's PSA level is between 20.1 and 30.0)+(4 if subject's PSA level is 30.1 or higher)    (Algorithm IV)

In certain aspects, the detection of one or more diagnostic miRNA may be incorporated into an existing prostate cancer prediction algorithm, such as the CAPRA score described in Cooperberg, et al. (2005) *J. Urol.* 173(6):1938-1942; the disclosure of which is incorporated herein by reference. For example, FIG. 8, Panel B shows modified CAPRA scores produced by adding one point to the score for each positive diagnostic miRNA (considering only mir-19a, mir-19b, and mir-519c-5p), where positivity is detection of a value exceeding the median detectable value. The resulting score (miRNA+CAPRA) displayed a significant increasing linear trend (p<0.001) in outcome risk, with 100% of the 12 individuals scored at the highest level (5) classified as cases. The detection of one or more diagnostic miRNA may be incorporated into other existing predictive tools, including nomograms, multivariable models, and the like. Predictive tools of interest include, but are not limited to, those described in Shariat S F, et al. (2008) *Curr. Opin. Urol.* 18(3):279-296 and Shariat S F, et al. (2008) *Cancer.* 113 (10:3075-3099; the disclosures of which are incorporated herein by reference.

In certain aspects, combination of the detection of one or more diagnostic miRNA (e.g., mir-19a, mir-19b, mir-519c-5p, mir-345, or any combination thereof) with an existing tool may use a statistical and/or learning machine algorithm(s) to find an optimal combination of the one or more diagnostic miRNA(s) with the other factor(s) considered by the prediction tool. A variety of statistical or machine learning algorithms are known in the art and may facilitate such a combination, such as genetic algorithms, support vector machines, neural networks, hidden Markov models, Bayesian networks, and the like.

Reports

The methods of the present disclosure can include generating a report indicating the results of the method and providing guidance as to how the results might be applied to the care of the subject. A "report," as described herein, refers generally to an electronic document or file (e.g., pdf file, monitor display), as well as a tangible document (e.g., paper report). A subject report can be completely or partially electronically generated, e.g., presented on an electronic display (e.g., computer monitor).

The method results in the report can include, for example, one or more of the amount of the diagnostic miRNA assayed. The level can be reported as a quantitative score (e.g., a concentration, e.g., pg/ml serum) and/or a semi-quantitative score (e.g., a score reflecting an amount of a biomarker relative to a control level or a selected threshold level). The method results can optionally include assay results for a control biomarker.

Reports can include information such as a predicted risk that the patient has or will develop an adverse prostate cancer pathology.

Reports can include guidance to a clinician as to a treatment recommendation for the subject based on the likelihood of adverse prostate cancer pathology in a subject. For example, reports can include a recommendation regarding further evaluation and/or avoiding expensive and invasive evaluations and/or a recommendations regarding therapeutic intervention (e.g., administering a drug, recommending surgical intervention, etc.), modifying a treatment regimen (e.g., adjusting a drug dose (e.g., increasing or decreasing a dose), adjusting a dosage regimen (e.g., increasing or decreasing dose frequency and/or amount), and the like.

A report can further include one or more of: 1) patient information (e.g., name, medical information (e.g., age, gender, symptoms (e.g., symptoms that may be relevant to diagnosis of prostate cancer), etc.), 2) information about the biological sample (e.g., type, when obtained); 3) information regarding where and how the assay was performed (e.g., testing facility, assay format); 4) service provider information; and/or 5) an interpretive report, which can provide a narrative providing an at least partial interpretation of the results so as to facilitate a diagnosis by a clinician.

Accordingly, the methods disclosed herein can further include a step of generating or outputting a report providing the method results and, optionally, other information such as treatment guidance as described herein. The report can be provided in the form of an electronic medium (e.g., an electronic display on a computer monitor), or in the form of a tangible medium (e.g., a report printed on paper or other tangible medium). An assessment as to the likelihood can be referred to as "risk report" or, simply, a "diagnostic result". The person or entity that prepares a report ("report generator") may also perform steps such as sample gathering, sample processing, and the like. Alternatively, an entity other than the report generator can perform steps such as sample gathering, sample processing, and the like. A report can be provided to a user. A "user" can be, for example, a health professional (e.g., a clinician, a laboratory technician, a physician, etc.).

Computer-Implemented Methods, Systems and Devices

The methods of the present disclosure can be computer-implemented, such that method steps (e.g., assaying, comparing, calculating, and the like) are be automated in whole or in part. Accordingly, the present disclosure provides methods, computer systems, devices and the like in connection with computer-implemented methods of determining a likelihood of adverse prostate cancer pathology in a subject.

For example, the method steps, including obtaining values for the diagnostic miRNA(s), comparing diagnostic miRNA amount(s) to a reference amount, generating a report, and the like, can be completely or partially performed by a computer program product. Values obtained can be stored electronically, e.g., in a database, and can be subjected to an algorithm executed by a programmed computer.

For example, the methods of the present disclosure can involve inputting the amount of a diagnostic miRNA (e.g., an amount of mir-19a, mir-19b, mir-519c-5p, and/or mir-345) into a computer programmed to execute an algorithm to perform the comparing step described herein, and generate a report as described herein, e.g., by displaying or printing a report to an output device at a location local or remote to the computer.

The present invention thus provides a computer program product including a computer readable storage medium having a computer program stored on it. The program can, when read by a computer, execute relevant calculations based on values obtained from analysis of one or more biological sample from an individual. The computer program product has stored therein a computer program for performing the calculation(s).

The present disclosure provides systems for executing the program described above, which system generally includes: a) a central computing environment; b) an input device, operatively connected to the computing environment, to receive patient data, wherein the patient data can include, for example, biomarker level or other value obtained from an assay using a biological sample from the patient, as described above; c) an output device, connected to the computing environment, to provide information to a user (e.g., medical personnel); and d) an algorithm executed by the central computing environment (e.g., a processor), where the algorithm is executed based on the data received by the input device, and wherein the algorithm calculates a value, which value is indicative of the likelihood the subject has an adverse prostate cancer pathology, as described herein.

Computer Systems

The present disclosure also provides computer systems for determining a likelihood of adverse prostate cancer pathology in a subject. The computer systems include a processor and memory operably coupled to the processor, where the memory programs the processor to receive assay data including an amount of at least one diagnostic miRNA in a biological sample from a subject; compare the amount received with a reference amount; and calculate a likelihood of adverse prostate cancer pathology in the subject, based on results of said comparing the determined amounts obtained from the analyzing unit with the reference amount. In certain aspects, the system calculates a likelihood of adverse prostate cancer pathology in the subject based on one or more additional risk factors, such as the subject's age, PSA level, etc.

Computer systems may include a processing system, which generally comprises at least one processor or processing unit or plurality of processors, memory, at least one input device and at least one output device, coupled together via a bus or group of buses. In certain embodiments, an input device and output device can be the same device. The memory can be any form of memory device, for example, volatile or non-volatile memory, solid state storage devices, magnetic devices, etc. The processor can comprise more than one distinct processing device, for example to handle different functions within the processing system.

An input device receives input data and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data can come from different sources, for example keyboard instructions in conjunction with data received via a network.

Output devices produce or generate output data and can comprise, for example, a display device or monitor in which case output data is visual, a printer in which case output data is printed, a port for example a USB port, a peripheral component adaptor, a data transmitter or antenna such as a modem or wireless network adaptor, etc. Output data can be distinct and derived from different output devices, for example a visual display on a monitor in conjunction with data transmitted to a network. A user can view data output, or an interpretation of the data output, on, for example, a monitor or using a printer. The storage device can be any form of data or information storage means, for example, volatile or non-volatile memory, solid state storage devices, magnetic devices, etc.

In use, the processing system may be adapted to allow data or information to be stored in and/or retrieved from, via wired or wireless communication means, at least one database. The interface may allow wired and/or wireless communication between the processing unit and peripheral components that may serve a specialized purpose. In general, the processor can receive instructions as input data via input device and can display processed results or other output to a user by utilizing output device. More than one input device and/or output device can be provided. A processing system may be any suitable form of terminal, server, specialized hardware, or the like.

A processing system may be a part of a networked communications system. A processing system can connect to a network, for example the Internet or a WAN. Input data and output data can be communicated to other devices via the network. The transfer of information and/or data over the network can be achieved using wired communications means or wireless communications means. A server can facilitate the transfer of data between the network and one or more databases. A server and one or more databases provide an example of an information source.

Thus, a processing computing system environment may operate in a networked environment using logical connections to one or more remote computers. The remote computer may be a personal computer, a server, a router, a network PC, a peer device, or other common network node, and typically includes many or all of the elements described above.

Certain embodiments may be described with reference to acts and symbolic representations of operations that are performed by one or more computing devices. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, personal digital assistants, multiprocessor systems, microprocessor-based systems, programmable consumer electronics, network, minicomputers, server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media including memory storage devices.

Computer Program Products

The present disclosure provides computer program products that, when executed on a programmable computer such as that described above, can carry out the methods of the present disclosure. As discussed above, the subject matter described herein may be embodied in systems, apparatus, methods, and/or articles depending on the desired configuration. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g. video camera, microphone, joystick, keyboard, and/or mouse), and at least one output device (e.g. display monitor, printer, etc.).

Computer programs (also known as programs, software, software applications, applications, components, or code) include instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, etc.) used to provide machine instructions and/or data to a programmable processor, including a machine-readable medium that receives machine instructions as a machine-readable signal.

It will be apparent from this description that aspects of the present invention may be embodied, at least in part, in software, hardware, firmware, or any combination thereof. Thus, the techniques described herein are not limited to any specific combination of hardware circuitry and/or software, or to any particular source for the instructions executed by a computer or other data processing system. Rather, these techniques may be carried out in a computer system or other data processing system in response to one or more processors, such as a microprocessor, executing sequences of instructions stored in memory or other computer-readable medium including any type of ROM, RAM, cache memory, network memory, floppy disks, hard drive disk (HDD), solid-state devices (SSD), optical disk, CD-ROM, and magnetic-optical disk, EPROMs, EEPROMs, flash memory, or any other type of media suitable for storing instructions in electronic format.

In addition, the processor(s) may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices. In alternative embodiments, special-purpose hardware such as logic circuits or other hardwired circuitry may be used in combination with software instructions to implement the techniques described herein.

Examples of Applications of Method Results

The methods of the present disclosure can provide results which can then be applied to facilitate decisions as to the care of the subject. Examples are provided below.

Assay-Guided Therapy and Monitoring of Therapy

The methods of the present disclosure can help a clinician in making a treatment decision for the subject, e.g., whether the results of the method suggest the subject may or may not benefit from invasive therapeutic intervention for treatment of prostate cancer. For example, based on the method results, a therapy can be selected for the subject based on the likelihood he has or is at risk of having an adverse prostate cancer pathology. Clinical signs, symptoms and other factors such as family history can also be considered to facilitate selecting a therapy.

The method results can guide a clinician as to whether or not any therapy for treatment of prostate cancer should be administered.

The methods of the present disclosure can facilitate monitoring therapy of a subject undergoing treatment for prostate cancer, such as watchful waiting, active surveillance, and the like. For example, where the subject is already receiving a therapy, the method can provide a method of monitoring therapy. In this case, the method results can guide a clinician in adjusting therapy (e.g., whether or not to continue therapy (e.g., so as to avoid relapse), increase or decrease dose, change therapy regimen (e.g., from monotherapy to combination therapy, or from non-surgical therapy to surgical therapy) where the patient is not receiving adequate therapeutic benefit (e.g., the patient is not responding to therapy), and the like). Such methods of monitoring therapy are useful in guiding further treatment decisions, such as whether continued administration of a drug regimen indicated, or whether the patient should receive a radical prostatectomy. The methods of monitoring therapy using the algorithms of the present disclosure may be used in combination with other methods for assessing whether a subject responds to therapy (is a "responder") or is not exhibiting a sufficient therapeutically beneficial response (is as "non-responder").

Identifying Subjects for Clinical Trial Populations

The methods of the present disclosure find use in identifying subjects suitable for inclusion or exclusion in a clinical trial based on upon the likelihood the subject has adverse prostate cancer pathology. For example, the methods of the present disclosure can be used to identify subjects suitable for inclusion in a clinical trial to assess efficacy of active surveillance on subjects that do not have adverse prostate cancer pathology, so that subjects that have adverse prostate cancer pathology are excluded. In another example, the methods of the present disclosure can be used to identify subjects having adverse prostate cancer pathology so as to exclude such subjects from a clinical trial (e.g., where the clinical trial is to assess efficacy of a drug for prostate cancer in subjects without adverse prostate cancer pathology). In another example, the methods of the present disclosure can be used to identify subjects suitable for inclusion in a clinical trial. Accordingly, such methods can facilitate identification of drugs or other therapies for treatment of prostate cancer in subjects with or without adverse prostate cancer pathology.

Kits

Kits of the present disclosure can include a detection agent(s) for one or more, two or more, three or more, or four or more diagnostic miRNAs. As used herein, a "detection reagent" refers to a binding partner for a biomarker that is suitable for use in detection of a biomarker, and is optionally detectably labeled. Detection agent(s) for one or more reference miRNA(s) can also be included. Kits can include one or more devices, computer systems, devices and the like, including such devices and computer systems as described herein.

Kits can include instructions for using the components of the kit to practice a method of the present disclosure. The instructions are generally recorded on a suitable recording medium, such as paper, plastic, electronic storage, medium, and the like. For example, the instructions may be present in the kits as a package insert, in the labeling of the container of the kit or components thereof (e.g., associated with the packaging or sub-packaging), etc. In other embodiments, the instructions are present as an electronic storage data file present on a suitable computer readable storage medium, e.g. compact disc-read only memory (CD-ROM), digital versatile disk (DVD), diskette, etc. In other examples, the instructions provided do not contain many or all assay details, but rather provide direction as to a remote source for obtaining detailed instructions, e.g. via the internet.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

Materials and Methods

The following are general materials and protocols used in the Examples below.

Study Design and Sample Collection

A schematic of the study design is depicted in FIG. 1. The study design followed the principle of prospective specimen collection and retrospective blinded evaluation (PRoBE) design. Serum and tissue samples were collected with informed consent from UCSF radical prostatectomy patients under institutional review board supervision and stored in the UCSF tissue core. Serum samples were collected at the time of surgery after induction of anesthesia but prior to any procedural intervention and stored at −80° C. until use. Formalin-fixed, paraffin-embedded (FFPE) radical prostatectomy tissue blocks were archived and available for analysis.

Patient Cohorts

Patients included in the study met the UCSF low-risk criteria for AS including biopsy Gleason 2-6 (no pattern 4 or 5), PSA less than 10 ng/ml, less than 33% of biopsy cores involved, less than 50% involvement in any single core, and clinical T1-T2 stage disease. All selected patients chose to undergo immediate radical prostatectomy. A Gleason score of 7 of higher was used to define adverse prostate cancer pathology.

The discovery cohort consisted of 48 patients with a post-surgical specimen Gleason score ≥7 (case group) and 48 patients with a post-surgical specimen Gleason score of 6 (control group). A validation cohort consisted of 46 patients in case and 50 25 patients in control group.

Detection of miRNAs miRNAs were detected using a microfluidic-based multiplex qRT-PCR method as described in Moltzahn, et al. (2010) Cancer Res. 71:550-560 and Moltzahn et al. (2011) J. Vis. Exp. 2011 Aug. 3(54), the disclosures of which are incorporated herein by reference. Briefly, total RNA was extracted from serum samples (300 µl) using the mirVana PARIS kit (Ambion) and concentrated using Amicon Ultra 0.5 3K centrifugal filter devices (Milipore). Multiplex reverse transcription reactions were performed on extracted RNA using stem-loop primers. The reverse transcription products were amplified utilizing unique forward primers and a universal reverse primer. Purification of the pre-PCR product was performed using the MinElute PCR purification kit (Qiagen). High throughput qPCR was performed on the purified product using a 96.96 Dynamic Array (Fluidigm). qPCR assays included individual forward primers, individual Taqman probes, and a universal reverse primer. The arrays were run on the BioMark system (Fluidigm). Libraries for 672 stem-loop primers, forward primers, and Taqman probes representing most known human miRNAs sequences were utilized (FIG. 19). Each array evaluated the expression of 96 miRNAs for 96 samples. A total of 7 arrays were performed on the discovery cohort (672 miRNA assays). One array was performed on the validation cohort focusing on those miRNAs detected in the discovery cohort.

Threshold cycle (Ct) values and amplification plots were obtained from proprietary software on the BioMark system (Fluidigm). Ct values were confirmed through quality analysis of amplification plots. miRNAs with a high Ct value (Ct>30) in >70% of the samples were deemed undetected and excluded from the analysis. Normalization was performed to the median Ct value of all detected miRNAs for each individual patient, resulting in a ΔCT value. The identity of the samples was masked until ΔCT values were obtained.

Statistical Analysis

Initial exploratory analyses compared distributions of normalized ΔCt values from miRNAs between cases and controls in the discovery sample, using graphical summaries and the Wilcoxon rank-sum test to assess significance. Models were developed for prediction of disease status using miRNAs with detectable normalized ΔCt values. Logistic regression models were initially fitted to candidate miRNAs singly, adjusting for age, PSA, and stage. Observed values for these miRNAs that exceeded the limit of detection were set at the limit. Candidate miRNAs were included in models both as continuous measures, and as binary categorical variables. Cut-off values for the latter were determined using separate classification tree models for each miRNA. An alternate cut-off defined by the median value among detectable values for each measure was also considered. Prediction performance of models was distinguished using receiver operating characteristic (ROC) area under the curve (AUC) values. A separate analysis based on a random forest classification model—as described in Hothron, et al. (2006) *J. Comp. and Graph. Stat.* 15: 651-674; the disclosure of which is incorporated herein by reference—was also conducted including all detectable miRNAs as well as age, PSA, and stage as predictors. The results of these analyses were used to provide an independent assessment of variable importance, and for confirmation of results from the simpler logistic models.

Confirmatory analyses were performed using the validation sample, and were based on the subset of miRNAs with detectable values that were also detectable in the discovery cohort. Because normalization procedures were performed separately in the two cohorts, ΔCt values for a given miRNA differed somewhat between groups. Therefore, prediction models developed in the validation sample could not be applied directly to predict outcomes among validation cases and controls. For this reason, validation analyses focused on assessing consistency of findings between the two cohorts by applying the same analytic approaches in each. Results were compared in terms of ROC assessments and variable importance rankings. In addition, the use of miRNAs to supplement the CAPRA score—as described in Cooperberg, et al. (2005) *J. Urol.* 173(6):1938-1942; the disclosure of which is incorporated herein by reference—as an index of disease risk was investigated. All statistical analyses were performed using R (version 2.15) and Stata (version 12.1).

In Situ Hybridizations

For in situ hybridizations, sections (5 μm) of FFPE patient tumor samples were stained using double DIG-labeled locked-nucleic acid (LNA) probes (Exiqon). Briefly, slides were deparaffinized, hydrated, proteinase K treated and then hybridized overnight to denatured probes at 54° C. in situ hybridization buffer (Enzo Life Sciences). Slides were washed in decreasing SSC concentrations, blocked, incubated with AP-conjugated anti-DIG (Roche), stained with BM Purple AP substrate (Roche), and counter stained with Nuclear-Fast Red (Vector). The pathologist who evaluated and graded the slides was blinded to patient diagnosis.

Example 1: Detection of Serum miRNAs Using Multiplex qRT-PCR

Multiplex qRT-PCR on a microfluidics platform provides an accurate and reliable approach for detecting serum miRNAs. This method was used to evaluate 672 miRNAs in serum of 96 patients with pre-surgical low risk disease (PSA<10, Gleason<7 with no 4+2, clinical stage <T3), but chose surgery over AS. Upon post-surgical pathological evaluation of the prostates, half of these patients had confirmed Gleason 6 ('control') while the other half were upgraded to Gleason 7 ('case'). Clinical characteristics of the patients are summarized in FIG. 2. Notably, there were no statistically significant differences in race, PSA, or clinical stage between the case and control groups. The case group did have a significantly higher age than the control group (p=0.009).

Detectable Ct values were demonstrated for 36 of the 672 miRNAs in at least 70% of the patients (FIG. 3). Many miRNAs exist as clusters, where two or more miRNAs are produced from a single transcript. Interestingly, nine of the 36 miRNAs detected in the serum of the discovery cohort are members of a single cluster, the miR17-92 cluster. MiRNAs are also grouped into families based on a common sequence at their 5' end called the seed sequence. This seed sequence largely determines the downstream messenger RNA targets of the miRNAs. Therefore, miRNAs with common seed sequence have many overlapping targets. miR-17, miR-20a, miR-92a, and miR-106a are all part of one family. Having multiple miRNAs from a single family supports a functional role for these miRNAs in these patients.

Example 2: Comparison of miRNA Serum Levels Between Case and Control Groups of the Discovery Cohort The serum levels of the detected miRNAs were compared between the case and control groups of the discovery cohort. Four of the detected miRNAs demonstrated differences in serum levels between the cases and controls. Mir-19b and mir-19a had significantly lower ΔCt values in the case group when compared to the controls (FIG. 4, Panels A-B; p=0.008 and p=0.023, respectively 2), showing higher serum expression in the case group. Conversely, mir-519c-5p and mir-345 had significantly higher ΔCt values in the case group when compared to the controls (FIG. 4, Panels C-D; p=0.013 and p=0.008, respectively), showing lower serum expression in the case group.

Figures 6, 7:
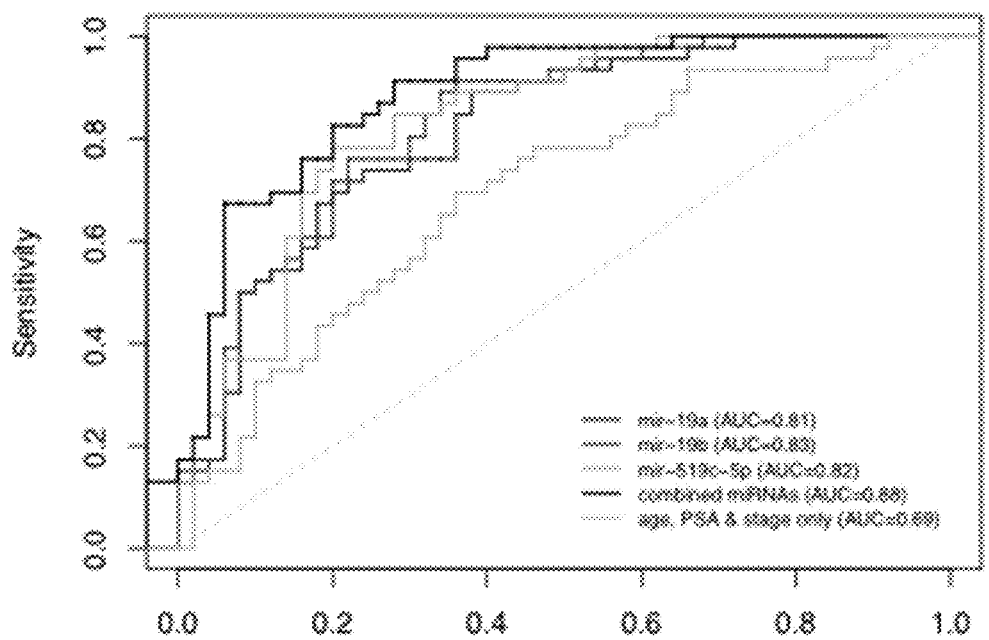
FIG. 6, Panels A-B are tables providing summaries of logistic regression models for individual miRNAs in the discovery (Panel A) and validation cohorts (Panel B).
FIG. 7 depicts ability of miRNAs to predict significant disease. ROC curves were constructed based on logistic regression models adjusting for age, stage and PSA. When used individually, mir-19b demonstrated reasonably good discriminatory ability with an AUC value of 0.83. Mir-19a and mir-519c-5p each showed similar discriminatory ability with AUC values of 0.82 and 0.81, respectively. The confirmed miRNAs each demonstrated improved predictive ability compared to the model including only age, PSA, and stage (which had an AUC value of 0.69). Furthermore, when the all three miRNAs were added to the model including these clinical characteristics, the AUC value improved to 0.88, showing additional value over current prediction tools.

Logistic regression models for predicting case/control status based on single miRNAs represented as binary indicators confirmed the significance results stated above, and these four miRNAs remained significant predictors of outcome status even when controlling for age, PSA, and disease stage (FIG. 6, Panel A). Results were not sensitive to whether miRNAs were included in prediction models as continuous variables, or as binary indicators based on median detectable levels. A nonparametric random forest classification including all detectable miRNAs as well as age, PSA, and disease stage ranked the following predictor variables as the five most important (in descending order): age, mir-19b, mir-519c-5p, mir-345 and mir-19a. None of the remaining miRNAs were significantly associated with outcome status.

Example 3: Comparison of miRNA Serum Levels Between Case and Control Groups of a Validation Cohort A validation study was performed to measure the altered microRNAs in an independent cohort with similar clinical and pathological characteristics to the discovery cohort. The patient characteristics for the validation cohort are summarized in FIG. 2. Similar to the discovery cohort, there were no statistically significant differences in race, PSA, or clinical stage between cases and controls. However, the case group was significantly older than the control group (p=0.002).

Figure 5:
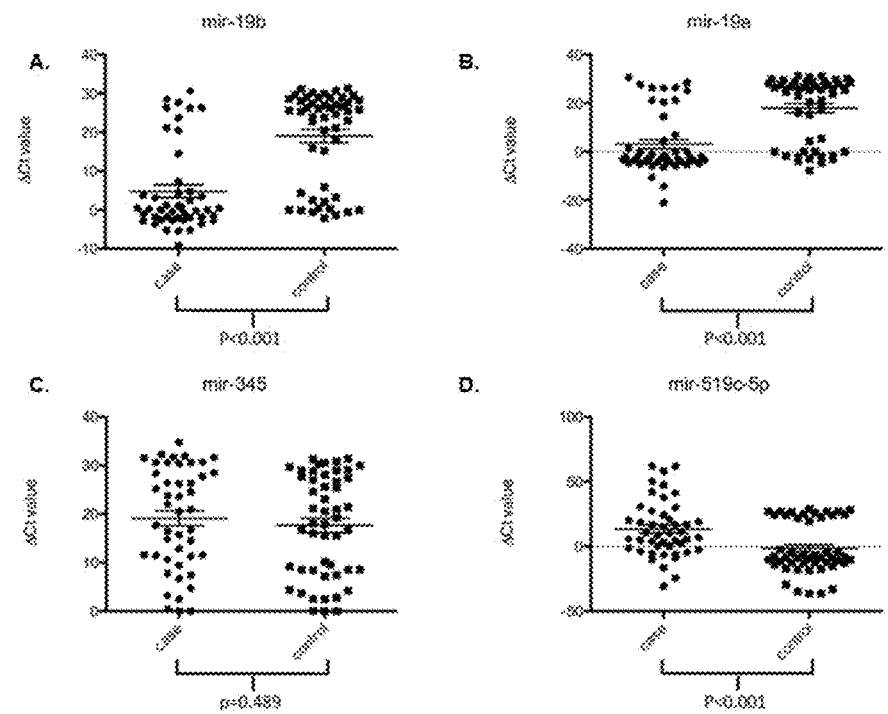
FIG. 5, Panels A-D depict miRNAs with differences in serum from the validation cohort. As seen in the discovery cohort, mir-19b (Panel A) and mir-19a (Panel B) showed significantly lower ΔCt values in the case group compared to the controls (p<0.001 for each). Indeed, the differences were even more striking in the validation cohort, likely due to normalization to the 36 expressed miRNAs rather than the 672 miRNAs measured in the discovery cohort. Serum levels of mir-519c-5p were also consistent with the previous results, showing significantly higher ΔCt values in the case group (Panel D; p<0.001). While the ΔCt values for mir-345 were similar to the results in the discovery cohort, the differences found between the cases and controls were not statistically significant (Panel C; p=0.489).

For the validation cohort, only those miRNAs found in the serum of the discovery cohort of patients (FIG. 3) were measured. As seen in the discovery cohort, mir-19b and mir-19a showed significantly lower ΔCt values in the case group compared to the controls (FIG. 5, Panels A-B; p<0.001 for each). Indeed, the differences were even more striking in the validation cohort. Serum levels of mir-519c-5p were also consistent with the previous results, showing significantly higher ΔCt values in the case group (FIG. 5, Panel D; p<0.001). While the ΔCt values for mir-345 were similar to the results in the discovery cohort, the differences found between the cases and controls were not statistically significant (FIG. 5, Panel C; p=0.489). In addition, mir-1274a, mir-92a, mir-93, mir-106a, mir-197, mir-486 and mir-720 had significantly different serum levels between cases and controls, all results that differed from those observed for the discovery cohort.

Example 4: Ability of miRNAs to Discriminate Patients with Adverse Prostate Cancer Pathology To evaluate the ability of the confirmed miRNAs to discriminate patients with adverse prostate cancer pathology, ROC curves for were constructed based on logistic regression models adjusting for age, stage and PSA (FIG. 6, Panel B, and FIG. 7). When used individually, mir-19b demonstrated reasonably good discriminatory ability with an AUC value of 0.83 (FIG. 7). Mir-19a and mir-519c-5p each showed similar discriminatory ability with AUC values of 0.81 and 0.82, respectively. The confirmed miRNAs each demonstrated improved predictive ability compared to the model including only age, PSA, and stage (which had an AUC value of 0.69). Furthermore, when the all three miRNAs were added to the model including these clinical characteristics, the AUC value improved to 0.88, showing additional value over current prediction tools.

As a further exploration of the potential for miRNAs to supplement the predictive ability of standard variables, augmenting the CAPRA score (FIG. 8, Panel A) was investigated by adding one point to the score for each of the three miRNAs observed to exceed the binary cutoff value (FIG. 8, Panel B). The resulting score displayed a significant increasing linear trend (p<0.001) in outcome risk, with 100% of the 12 individuals scored at the highest level (5) classified as cases.

Example 5: In Situ Hybridizations

Figure 9:
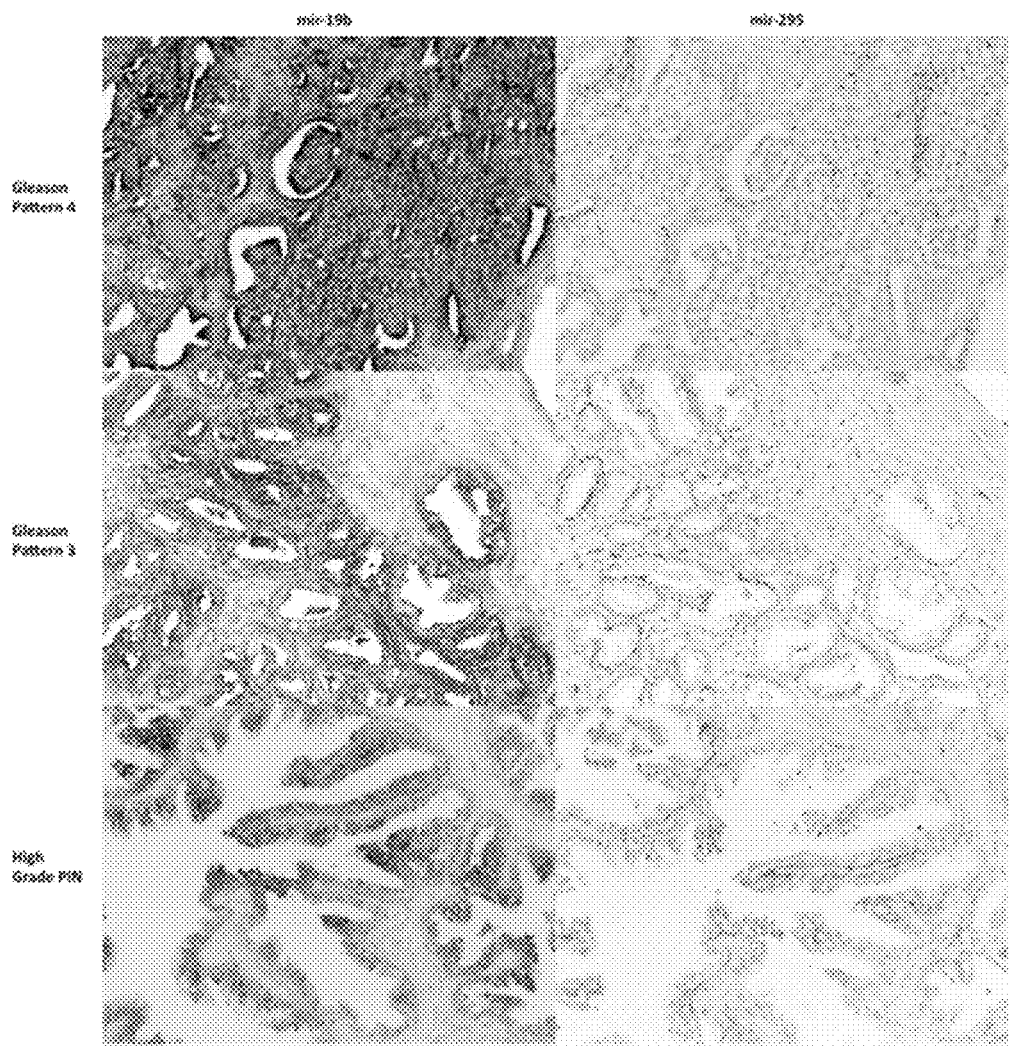
FIG. 9 depicts detection of miRNAs in patient prostate samples. In order to determine whether the predictive miRNAs are present in prostate tumors, in situ hybridizations were performed for miRNAs on FFPE tumor samples from patients in the cohort (n=10). Staining for mir-19b was detected in areas of high-grade PIN, Gleason pattern 3, and Gleason pattern 4. Areas of normal prostate epithelia and stromal tissue showed no detectable staining for mir-19b. In contrast, mir-519c-5p demonstrated variable staining in normal epithelial, abnormal prostate epithelia, and stromal tissue. There was no detectable staining for mir-295, a miRNA not expressed in human tissue.

The uncovered serum miRNAs may arise directly from the tumor or from the body's response to the tumor. In order to determine whether the predictive miRNAs are present in prostate tumors, in situ hybridizations were performed for miRNAs on FFPE tumor samples from patients in the cohort (n=10). Staining for mir-19b was detected in areas of high-grade PIN, Gleason pattern 3, and Gleason pattern 4 (FIG. 9). Areas of normal prostate epithelia and stromal tissue showed no detectable staining for mir-19b. In contrast, mir-519c-5p demonstrated variable staining in normal epithelial, abnormal prostate epithelia, and stromal tissue. There was no detectable staining for mir-295, a miRNA not expressed in human tissue (FIG. 9).

Upon completion of the study presented as Examples 1-5 above and FIGS. 1-9, it was discovered that certain samples in the validation cohort overlapped with samples in the discovery cohort due to an error at the tissue bank. To ensure the integrity of the results was not affected, a subsequent study was performed with no sample overlap. This study and the results thereof are presented as Example 6 below.

Example 6: Predicting Adverse Pathology in Prostate Cancer Patients Eligible for Active Surveillance Study Design The study design followed the principle of prospective specimen collection and retrospective blinded evaluation (PRoBE) design and reported following the REMARK guidelines. All serum samples were collected routinely at the time of surgery after induction of anesthesia but prior to any procedural intervention and stored at −80° C. until use. Formalin-fixed, paraffin-embedded (FFPE) radical prostatectomy tissue blocks were archived and available for analysis.

Figures 10, 11:
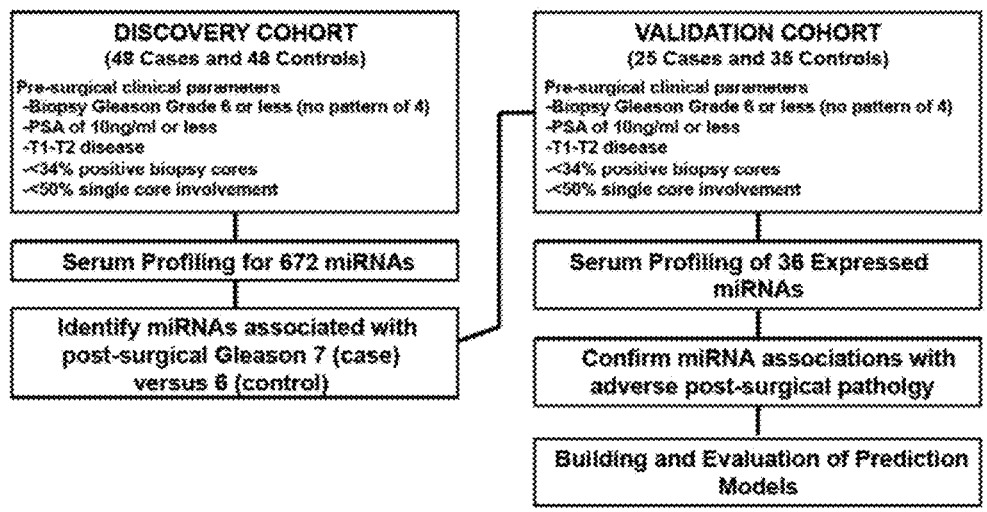
FIG. 10 is a schematic of the design of a second study. Patients met the UCSF low-risk criteria for AS including biopsy Gleason 2-6 (no pattern 4 or 5), PSA less than 10 ng/ml, less than 34% of biopsy cores involved, less than 50% involvement in any single core, and clinical T1-T2 stage disease. All selected patients chose to undergo immediate radical prostatectomy. A Gleason score of 7 of higher was used to define adverse prostate cancer pathology. The discovery cohort consisted of 48 patients with a post-surgical specimen Gleason score >7 (case group) and 48 patients with a post-surgical specimen Gleason score of 6 (control group). A validation cohort consisted of 25 patients in the case and 35 patients in the control group.
FIG. 11 is a table listing patient characteristics of the discovery and validation cohorts in the second study.

Patients included in the study were those opting for immediate radical prostatectomy who met the UCSF low-risk criteria for AS including biopsy Gleason 2-6 (no pattern 4 or 5), PSA less than 10 ng/ml, less than 34% of biopsy cores involved, less than 50% involvement in any single core, and clinical T1-T2 stage disease. A pathologic Gleason score of 7 of higher is associated with an increased risk of PCa mortality and, therefore, was used to define adverse pathology. The discovery cohort consisted of 48 patients with a post-surgical pathologic Gleason score of 7 or higher (case group) and 48 patients with a pathologic Gleason score of 6 (control group). A validation cohort consisted of 25 cases and 35 controls. Patients were chosen from available samples maintained in a UCSF tissue bank. Patients fitting criteria above were selected from the available pool based on a random integer generator. A schematic of the study design is depicted in FIG. 10.

Microfluidics-Based Multiplex qRT-PCR Profiling of miRNAs

A microfluidic-based multiplex qRT-PCR method was used to detect miRNAs as previously described. Libraries for 672 stem-loop primers, forward primers, and Taqman probes representing most known human miRNAs sequences (sequences at http://urology.ucsf.edu/blellochlab/protocols/miRNAqPCRsequences.txt) were used. Each microfluidic array evaluated the expression of 96 miRNAs for 96 samples. A total of 7 arrays were performed on the discovery cohort (672 miRNA assays). One array was performed on the validation cohort focusing only on those miRNAs detected (see below) in the discovery cohort.

Amplification plots and threshold cycle (Ct) values, a measure of the number of PCR cycles to reach a threshold line set within the exponential phase of amplification, were obtained from proprietary software on the BioMark system (Fluidigm). A higher Ct reflects lower input of measured miRNA. Ct values were confirmed through quality analysis of amplification plots. MiRNAs with a high Ct value (Ct>30) in >70% of the samples were deemed undetected and excluded from the analysis. Normalization was performed to the median Ct value of all detected miRNAs within an array for each individual patient, resulting in a ΔCT value (FIGS. 11 and 12). Normalization was performed to account for systematic variations in miRNA expression levels across individuals and arrays, so that biological differences can be more easily distinguished. However, analysis of un-normalized data, simply controlled for amount of input serum led to analogous findings. The identity of the samples was masked until ΔCT values were obtained.

Statistical Analysis

Initial analyses compared distributions of normalized ΔCT values from miRNAs between cases and controls in the discovery sample using graphical summaries and the Wilcoxon rank-sum test to assess significance. Logistic regression models were then fitted to candidate miRNAs singly, adjusting for age, PSA, stage, and degree of biopsy involvement including percent cores tumor positive and percent of total length of cores involved. Candidate miRNAs were included in models both as continuous measures, and as binary categorical variables. Cut-off values for the latter were determined using separate classification tree models or by the median for each miRNA. Both cut-offs gave similar results.

Prediction performance of models was distinguished using receiver operating characteristic (ROC) area under the curve (AUC) values. A separate analysis based on a random forest classification model was also conducted including all detectable miRNAs as well as age, PSA, stage, and degree of biopsy involvement as predictors. The results of this analysis were used to provide an independent assessment of variable importance, and for confirmation of results from the simpler logistic models.

For the validation cohort, only those miRNAs that were detected in >30% of the samples in the discovery cohort were measured. Normalizing to all detected miRNAs run on a single array changed the breadth of ΔCT values for a given miRNA, often improving differences between cases and controls. Analytic approaches described above for discovery were similarly applied in the validation cohort. Final analyses focused on miRNAs detected as significant predictors in the discovery cohort that also were significant in the validation set. Only markers with adjusted p-values (based on false discovery rate methods) of at most 0.1 in discovery analyses were considered. These were modeled singly and jointly in logistic regression models also controlling for the same characteristics considered in analyses for the discovery cohort. In addition, we investigated the use of selected miRNAs to supplement the well-validated CAPRA score as an index of disease risk as described in more detail in results.

Additional descriptive analyses were conducted to compare selected patient characteristics between the discovery and validation cohorts. Formal testing was based on Fisher's Exact test (for categorical characteristics) and the Wilcoxon rank-sum test (for quantitative characteristics).

All statistical analyses were performed using R (version 2.15) and Stata (version 12.1).

In Situ Hybridizations

Slides with sections (5 µm) of FFPE tumor samples from the patient cohort were deparaffinized in Xylene and hydrated through decreasing ethanol concentrations into PBS. The slides were then treated with 300 µl of proteinase-K (15 µg/ml in PK buffer, 5 mM Tris-HCl pH 7.4, 1 mM EDTA, 1 mM NaCl) at 37° c. in a hybridizer (Dako) for 10 minutes. After two PBS washes, the sections were dehydrated through increasing ethanol concentrations and air-dried for 15 minutes. Double DIG-labeled locked-nucleic acid (LNA) probes (Exiqon) for individual miRNAs were denatured by heating at 90° c. for 4 minutes then diluted to 40 nM using in situ hybridization buffer (Enzo Life Sciences). The sections were hybridized with 50 µl of diluted probe at 54° C. overnight then washed in decreasing SSC concentrations at hybridization temperature. Following a 5 minute incubation in 0.2×SSC at room temperature, the slides were washed in PBS and blocked with 2% blocking solution (Roche) for 15 minutes. The sections were then treated with alkaline phosphatase (AP)-conjugated anti-DIG (Roche) diluted 1:800 in blocking solution containing 2% sheep serum for 60 minutes. After two washes in AP buffer (100 mM Tris ph 9.5, 50 mM $MgCl_2$, 100 mM NaCl, 0.1% Tween-20, 2 mM levamisol), the sections were incubated in BM Purple AP substrate (Roche) in the dark at 4° C. overnight. The slides were then washed twice in PBS containing 0.1% Tween-20 and washed twice in water. Following a 30 second treatment with Nuclear-Fast Red (Vector), the slides were dehydrated though increasing ethanol concentrations then mounted. The stained slides were evaluated and graded blindly.

Results miRNA Profiling in Discovery Cohort

We aimed to determine whether miRNAs from pre-surgical serum samples could predict post-surgical pathological upgrade. Clinical characteristics of the patients in our discovery cohort are summarized in FIG. 11. Case (post-surgical Gleason 7) and control (post-surgical Gleason 6) groups had similar distributions of race and clinical characteristics. Cases were significantly older than controls (p=0.005). PSA levels also were somewhat higher in cases (p=0.07). Of the 672 miRNAs tested, 36 had Ct<30 in at least 30% of the patients, which we established as a cutoff of detection (Table 2). Many miRNAs exist as clusters, where two or more miRNAs are produced from a single transcript. Nine of the 36 miRNAs are members of a single cluster, the miR17-92 cluster. MiRNAs are also grouped into families based on a common sequence at their 5' end called the seed sequence, which largely defines their downstream targets. miR-17, miR-20a, miR-92a, and miR-106a, for example, are all part of one family. Therefore, across all these PCa patients, there was an apparent enrichment for specific clusters and families of miRNAs.

Figure 16:
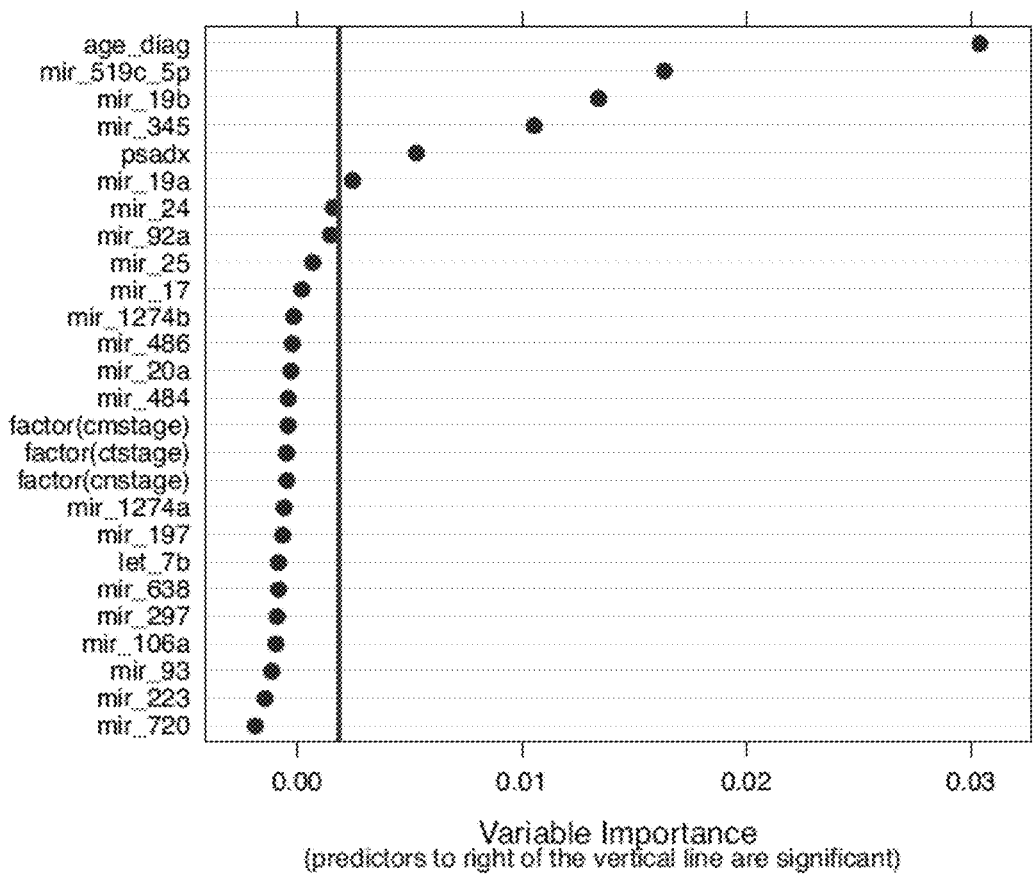
FIG. 16 shows a summary of variable importance values from a random forest model fitted to the discovery dataset. Included variables are listed on the vertical axis, with corresponding variable importance for each on the horizontal axis, Importance is determined using "conditional permutation accuracy", calculated as a the average difference in model accuracy between the fitted model and alternative versions obtained via random permutations of the variable values. Variables are considered significant predictors in the random forest if their variable importance value is above the absolute value of the lowest negative-scoring variable.

We next compared the serum levels of the 36 detected miRNAs between the case and control groups of the discovery cohort. Four of the detected miRNAs demonstrated differences in serum levels between the cases and controls. MiR-19a and miR-19b displayed lower ΔCt values in the case group compared to controls (FIG. 15, Panel A, p=0.06 and p=0.07 respectively), consistent with higher serum levels in cases. Conversely, miR-345 and miR-519c-5p had significantly higher ΔCt values in the case group when compared to the controls (FIG. 15, Panel A, p=0.04 and p=0.02 respectively), consistent with lower serum levels in the case group. Logistic regression models for predicting case/control status based on single miRNAs represented as binary indicators (with cut-off values selected using classification trees) showed all four miRNAs as highly significant predictors of outcome status (odds ratio) even when controlling for age, PSA, clinical stage, and degree of biopsy involvement (FIG. 13). Results were not sensitive to whether miRNAs were included in prediction models as continuous variables or as binary indicators based on median detectable levels (data not shown). A nonparametric random forest classifier including all detectable miRNAs (represented as continuous measures) as well as age, PSA, stage, and biopsy involvement ranked the following predictor variables as the six most important (in descending order): age, miR-519c-5p, miR_19 b, miR-345, PSA and miR_19a (FIG. 16). None of the other measured miRNAs were significantly associated with outcome status.

Validation of miRNA Signature in Independent Cohort

To confirm our miRNA associations, we performed a validation study focusing only on those miRNAs that were measure in at least 30% of patients' serum samples (FIG. 12). The patient characteristics for the validation cohort are summarized in Table 1. Similar to the discovery cohort, there were no statistically significant differences in race, or clinical stage between cases and controls, while differences in age and PSA were significant (p=0.002 and 0.04 respectively). As seen in the discovery cohort, miR-19b and miR-19a showed significantly lower ΔCt values in the case group compared to the controls (FIG. 15, Panel B). Indeed, the differences were even more striking in the validation cohort (p<0.001 for both), likely due to normalization based on all detected miRNAs on a single array (versus spread across multiple arrays in discovery cohort). Serum levels of miR-519c-5p were also consistent with the previous results, showing significantly higher ΔCt values in the case group (FIG. 15, Panel B, p=0.0022). While the ΔCt values for miR-345 were similar to the results in the discovery cohort, the differences found between the cases and controls were not statistically significant (FIG. 15, Panel B, p=0.3536). However, in models adjusting for age and PSA, miR-345 remained highly significant when included as a binary predictor (see below).

Prognostic Value of Three-miRNA Signature

To evaluate the ability of the confirmed miRNAs to discriminate patients with adverse pathology in the validation set, they were included in logistic regression models also adjusting for age, stage, PSA, and extent of biopsy involvement. When considered individually, all four miRNAs showed strong associations with case status, with odds ratios of 9.22, 12.67, 0.03 and 0.06 (p values <0.01) (FIG. 13). Furthermore they individually showed improved discriminatory ability with AUCs of 0.85, 0.86, 0.84, and 0.88 relative to an AUC of 0.77 for a model including only age, PSA, stage, and biopsy involvement, with miR-519c-5p yielding a statistically significant improvement at the 5% level (FIG. 13). Next we evaluated models using different combinations of the miRNAs (FIG. 14). Notably, miR-19a and miR-19b appeared to be co-dependent, consistent with the fact that they are expressed from a common transcript, miR-17-92. Remarkably, models consisting of a combination either miR-19a or miR-19b together with miR-345 and miR-519c-5p showed a AUC of 0.94 (p=0.007 and 0.009 respectively) (FIG. 14 and FIG. 17, Panel A).

In order to identify a scoring mechanism accessible to physicians and their patients, we evaluated the utility of adding miRNA values to an established risk model, the CAPRA score. Notably, our cohort had low CAPRA scores (ranging from 0-2 out of 10) as expected for AS-eligible patients. By adding one point to the score for each of the three miRNAs (miR-19a or 19b, miR-345, and miR-519c-5p) that was observed to exceed the binary cutoff value, patients could be separated into those likely to have Gleason 7—and hence intermediate risk—disease versus those that did not (FIG. 17, Panels B and C). The linear trend was highly significant (p<0.001). Indeed, 100% of patients (n=13) with a score of 4 or 5 had Gleason 7 disease post-surgically versus 2 out of 31 of patients with scores of 1 or 2.

Origin of Serum miRNAs

Figure 18:
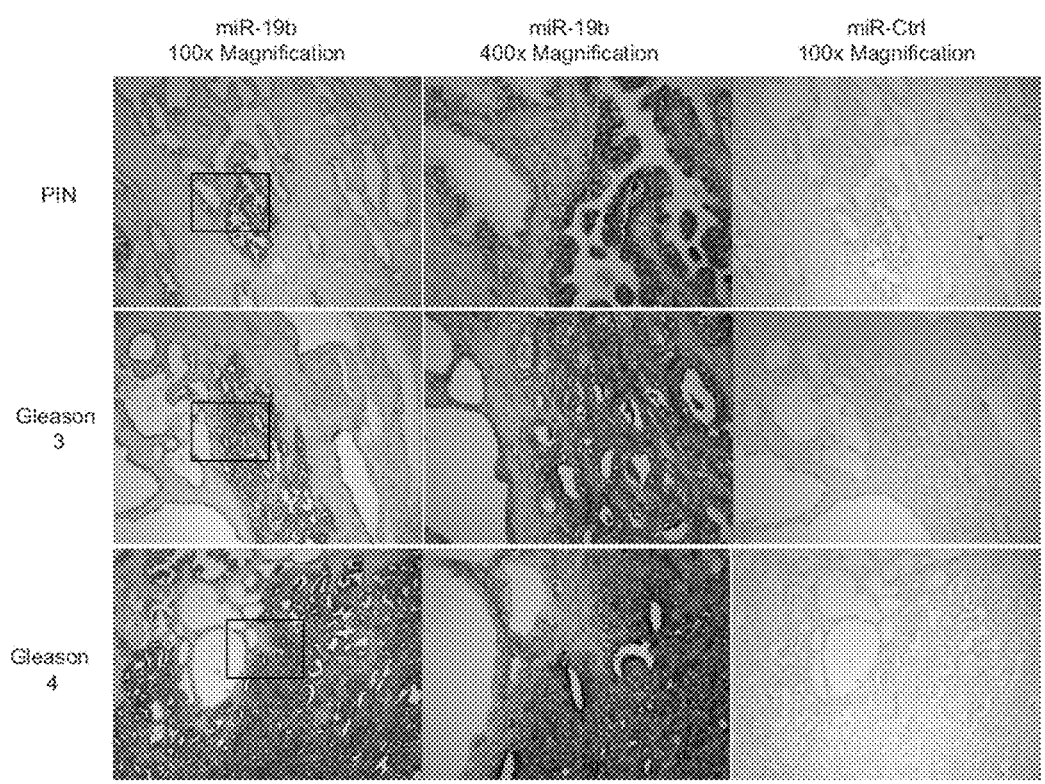
FIG. 18 shows staining for miR-19b in patient tumor samples. Images show in situ hybridization staining for miR-19b (left and center panels) and negative control, miR-295 (right panels). Top panels show area of prostate intraepithelial neoplasia (PIN). Middle panels show area of Gleason 3. Bottom panels show area of Gleason 4. Areas of PIN, Gleason 3, and Gleason 4 all stain strongly for miR-19b probe (blue staining). Note each panel has area of normal-appearing epithelium, most clearly seen on the left of each center panel. These areas show much lower staining. Right and left panels, 100× magnification. Center panels, 400× magnification. Center panels represent boxed areas in left panels.

The uncovered serum miRNAs may arise directly from the tumor or from the body's response to the tumor. In order to determine whether the predictive miRNAs are present in prostate tumors, we performed in situ hybridizations with probes for miR-19b and miR-519c-5p on FFPE tumor samples from patients in our cohort (n=10). Staining for miR-19b was strong in areas of high-grade PIN, Gleason pattern 3, and Gleason pattern 4, but absent in normal appearing epithelium (FIG. 18). However, there was no obvious difference in intensity of staining with increasing grade from PIN to Gleason pattern 4. In contrast, miR-519c-5p demonstrated variable staining in normal epithelial, abnormal prostate epithelia, and stromal tissue. In summary, while miR-19 cellular levels clearly increased with transformation, it was unclear if there was any further increase within the cells with pathological progression.

In conclusion, this study identifies for the first time a serum miRNA signature that can act as an independent prognostic marker in PCa. Furthermore, it shows how serum miRNAs can be used to identify relatively small steps in tumor progression allowing increasing clinical refinement of disease status.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09790557B2). An electronic copy of the "Sequence Listing" will also be available from the USPTO upon request and payment of the fee set forth in 37 CFR 1.19(b)(3).

What is claimed is:

1. A method comprising:
   determining an amount of each miRNA in a set of miRNAs consisting of:
   mir-19a, mir-519c-5p, and mir-345; or
   mir-19b, mir-519c-5p, and mir-345,
   in a sample of blood or blood product from a male human subject suspected of having prostate cancer, by
   a) reverse transcribing RNA from the sample using a primer that hybridizes with mir-19a, mir-19b, mir-519c-5p or mir-345, to generate a reverse transcription product encoding mir-19a, mir-19b, mir-519c-5p or mir-345 and
   b) detecting an amount of the reverse transcription product encoding mir-19a, mir-19b, mir-519c-5p or mir-345.

2. The method according to claim 1, comprising measuring the subject's PSA level.

3. The method according to claim 1, comprising biopsying the subject's prostate.

4. The method according to claim 1, wherein the blood product is serum or plasma.

5. The method according to claim 1, comprising obtaining the sample of blood or blood product from the subject.

6. The method according to claim 1, wherein the determining comprises performing quantitative real-time PCR to determine the amount of each miRNA in the set of miRNAs.

7. The method according to claim 6, wherein the quantitative real-time PCR is multiplexed.

8. The method according to claim 1, comprising administering prostate cancer therapy to the male human subject.

9. The method according to claim 1, wherein the male human subject is undergoing prostate cancer therapy.

10. The method of claim 1, wherein the primer is a stem loop primer.

11. The method according to claim 1, further comprising assaying an amount of one or more reference miRNAs in the sample of blood or blood product.

* * * * *